United States Patent
Albert et al.

(10) Patent No.: US 10,301,247 B2
(45) Date of Patent: *May 28, 2019

(54) METHODS OF MAKING ACRYLIC ACID FROM LACTIC ACID USING MOLTEN SALT CATALYSTS

(71) Applicants: The Procter & Gamble Company, Cincinnati, OH (US); Friedrich Alexander Universitat Erlangen-Nurnberg, Erlangen (DE)

(72) Inventors: Jakob Albert, Erlangen (DE); Peter Wasserscheid, Erlangen (DE); Nicola Taccardi, Erlangen (DE); Jens Nagengast, Erlangen (DE); Matthias Kehrer, Erlangen (DE); Julian Kadar, Erlangen (DE); Dimitris Ioannis Collias, Mason, OH (US)

(73) Assignees: The Procter & Gamble Company, Cincinnati, OH (US); Friedrich Alexander Universitat Erlangen-Nurnberg, Erlangen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/913,944

(22) Filed: Mar. 7, 2018

(65) Prior Publication Data
US 2018/0258024 A1    Sep. 13, 2018

Related U.S. Application Data

(60) Provisional application No. 62/616,010, filed on Jan. 11, 2018, provisional application No. 62/469,155, filed on Mar. 9, 2017.

(51) Int. Cl.
*C07C 51/377* (2006.01)
*C07C 51/363* (2006.01)
*B01J 31/02* (2006.01)

(52) U.S. Cl.
CPC .......... *C07C 51/377* (2013.01); *B01J 31/0298* (2013.01); *C07C 51/363* (2013.01); *Y02P 20/582* (2015.11)

(58) Field of Classification Search
CPC ... C07C 51/353; C07C 51/363; C07C 51/377; C07C 53/19; C07C 57/04; B01J 31/0298
See application file for complete search history.

(56) References Cited

U.S. PATENT DOCUMENTS 9,309,180 B2    4/2016   Kuppinger et al.

FOREIGN PATENT DOCUMENTS

WO    WO2017108890 A1    6/2017

OTHER PUBLICATIONS

International Search Report and Written Opinion for PCT/US2018/021322 dated Jun. 8, 2018.

*Primary Examiner* — Yate' K Cutliff
(74) *Attorney, Agent, or Firm* — James E Oehlenschlager

(57) ABSTRACT

A method of making acrylic acid in liquid phase by contacting a feed stream containing lactic acid, lactide, or mixtures thereof with a molten salt catalyst comprising a protic ionic liquid (PIL), which contains a bromide anion (Br⁻), is provided.

33 Claims, 2 Drawing Sheets

METHODS OF MAKING ACRYLIC ACID FROM LACTIC ACID USING MOLTEN SALT CATALYSTS

FIELD OF THE INVENTION

The present invention generally relates to a method of making acrylic acid in liquid phase from a feed stream comprising lactic acid, lactide, or mixtures thereof. More specifically, the method of the present invention comprises three steps: (a) contacting the feed stream with a molten salt catalyst comprising a protic ionic liquid (PIL), which contains a bromide anion (Br⁻), to produce 2-bromopropionic acid (2-BrPA) as an intermediate; (b) converting the 2-BrPA to a mixture of acrylic acid and 3-bromopropionic acid (3-BrPA) using a molten salt catalyst comprising an ionic liquid (IL), which contains a bromide anion (Br⁻); and (c) converting the 3-BrPA to acrylic acid using an amine.

BACKGROUND OF THE INVENTION

Acrylic acid, acrylic acid derivatives, or mixtures thereof are used today in a variety of industrial materials, such as adhesives, binders, coatings, paints, polishes, detergents, flocculants, dispersants, thixotropic agents, sequestrants, and superabsorbent polymers (SAP), which are used in disposable absorbent articles, including diapers and hygienic products. In terms of production process, acrylic acid is typically made today from the two-step catalytic oxidation of propylene, which in turn is produced from fossil resources, such as petroleum or natural gas. More on the oxidation of propylene to make acrylic acid and other production methods can be found in the Kirk-Othmer Encyclopedia of Chemical Technology, Vol. 1, pgs. 342-369 (5$^{th}$ Ed., John Wiley & Sons, Inc., 2004).

Fossil-derived acrylic acid uses resources that are not renewable as it takes hundreds of thousands of years to form naturally and only a short time to consume, and contributes to greenhouse emissions due to its high content of fossil-derived carbon. On the other hand, renewable resources refer to materials that are produced via a natural process at a rate comparable to their rate of consumption (e.g., within a 100-year time frame) and can be replenished naturally or via agricultural techniques. Examples of renewable resources include plants, such as sugar cane, sugar beets, corn, potatoes, citrus fruit, woody plants, lignocellulose, carbohydrate, hemicellulose, cellulosic waste, animals, fish, bacteria, fungi, and forestry products. As fossil resources become increasingly scarce, more expensive, and potentially subject to regulations for $CO_2$ emissions, there exists a growing need for non-fossil-derived acrylic acid, acrylic acid derivatives, or mixtures thereof that can serve as an alternative to fossil-derived acrylic acid, acrylic acid derivatives, or mixtures thereof.

Many attempts have been made over the last 80 years to make non-fossil-derived acrylic acid, acrylic acid derivatives, or mixtures thereof from renewable resources, such as lactic acid (also known as 2-hydroxypropionic acid) and other materials. From these resources, only lactic acid is produced today in high yield and purity from sugar (≥90% of theoretical yield, or equivalently, ≥0.9 g of lactic acid per g of sugar), and with economics which could support producing acrylic acid cost competitively to fossil-derived acrylic acid. As such, lactic acid or lactate presents a real opportunity of serving as a feedstock for bio-based acrylic acid, acrylic acid derivatives, or mixtures thereof.

The overwhelming majority of scientific literature and patent art describe the gas phase dehydration of lactic acid, lactic acid derivatives, or mixtures thereof to acrylic acid, acrylic acid derivatives, or mixtures thereof. However, liquid phase dehydration should offer significant advantages over the gas phase dehydration, for example, lower operating temperature and pressure, longer residence time, lower energy use and $CO_2$ emissions, wide selection of catalyst types (e.g. homogeneous and heterogeneous) and catalysts to choose from, lower coking potential of the catalysts, lower safety concerns, lower potential for lactic acid corrosion, wider selection of reactor designs, etc. U.S. Pat. No. 9,309,180 (assigned to Evonik Industries AG) discloses a process to dehydrate lactic acid and produce acrylic acid in liquid phase with the use of various metal salt catalysts, such as $K_2HPO_4$, $KH_2PO_4$, $BaHPO_4$, and mixtures of similar salts. At 300° C. and reaction time ranging from 4.4 h to 5.5 h, the yield of acrylic acid was between 0.1 mol % and 1.3 mol %.

Accordingly, there is a need for liquid phase dehydration methods of lactic acid, lactide, or mixtures thereof to acrylic acid with high yield and selectivity.

SUMMARY OF THE INVENTION

In one embodiment of the present invention, a method of making acrylic acid is provided. The method comprises the steps: (a) contacting a feed stream comprising lactic acid, lactide, or mixtures thereof with a first molten salt catalyst in a first reactor at a first reaction temperature and a first reaction time to produce 2-bromopropionic acid (2-BrPA); (b) contacting said 2-BrPA with a second molten salt catalyst in a second reactor at a second reaction temperature and a second reaction time to produce 3-bromopropionic acid (3-BrPA) and a first stream of said acrylic acid; and (c) contacting said 3-BrPA with an amine in a third reactor at a third reaction temperature and a third reaction time to produce a second stream of said acrylic acid; wherein said first molten salt catalyst comprises a bromide anion (Br⁻); wherein said second molten salt catalyst comprises a Br⁻; wherein first stream of said acrylic acid and said second stream of said acrylic acid are combined into a production stream of acrylic acid; and wherein said acrylic acid in said production stream has an overall acrylic acid yield and an overall acrylic acid selectivity.

In another embodiment of the present invention, a method of making acrylic acid is provided. The method comprises the steps: (a) contacting a feed stream comprising lactic acid, lactide, or mixtures thereof with a first molten salt catalyst in a first reactor at a reaction temperature of about 120° C. and a reaction time of about 5 h to produce a first stream comprising 2-bromopropionic acid (2-BrPA) at a yield of about 60 mol % and with a selectivity of more than 95 mol %; (b) contacting said 2-BrPA with a second molten salt catalyst in a second reactor at a reaction temperature of about 160° C. and a second reaction time of about 20 h to produce a second stream comprising 3-bromopropionic acid (3-BrPA) at a yield of about 79 mol % and with a selectivity of about 89 mol %, and said acrylic acid at a yield of about 3 mol %; and (c) contacting said 3-BrPA with a trioctylamine (TOA) in a third reactor at a third reaction temperature of about 180° C. and a third reaction time of about 0.5 h to produce a third stream comprising said acrylic acid at a yield of about 90 mol % and with a selectivity of more than about 90 mol %; wherein said first molten salt catalyst comprises 3-methyl-1-(4-butane sulfonic acid) imidazolium bromide ([MIMBS]Br); wherein said [MIMBS]Br has a molar ratio to said lactic acid, lactide, or mixtures thereof of about 3:1; wherein said molten salt catalyst further comprises a 20 mmol HBr aqueous solution; wherein said second molten salt catalyst comprises tetrabutylphosphonium bromide ([PBu$_4$]Br); wherein said [PBu$_4$]Br and said 2-BrPA have a molar ratio of about 1:1; wherein said acrylic acid of said second stream is combined with said acrylic acid of said third stream into a production stream of said acrylic acid; and wherein said acrylic acid in said production stream has an overall acrylic acid yield of about 43 mol % and an overall acrylic acid selectivity of about 76 mol %.

In yet another embodiment of the present invention, a method of making acrylic acid is provided. The method comprises the steps: (a) contacting a feed stream comprising lactic acid, lactide, or mixtures thereof with a first molten salt catalyst in a first reactor at a reaction temperature of about 120° C. and a reaction time of about 5 h to produce a first stream comprising 2-bromopropionic acid (2-BrPA) at a yield of about 60 mol % and with a selectivity of more than 95 mol %; (b) contacting said 2-BrPA with a second molten salt catalyst in a second reactor at a reaction temperature of about 180° C. and a second reaction time of about 3 h to produce a second stream comprising 3-bromopropionic acid (3-BrPA) at a yield of about 52 mol % and with a selectivity of about 54 mol %, and said acrylic acid at a yield of about 45 mol %; and (c) contacting said 3-BrPA with a trioctylamine (TOA) in a third reactor at a third reaction temperature of about 180° C. and a third reaction time of about 0.5 h to produce a third stream comprising said acrylic acid at a yield of about 90 mol % and with a selectivity of more than about 90 mol %; wherein said first molten salt catalyst comprises 3-methyl-1-(4-butane sulfonic acid) imidazolium bromide ([MIMBS]Br); wherein said [MIMBS]Br has a molar ratio to said lactic acid, lactide, or mixtures thereof of about 3:1; wherein said molten salt catalyst further comprises a 20 mmol HBr aqueous solution; wherein said second molten salt catalyst comprises tetrabutylphosphonium bromide ([PBu$_4$]Br); wherein said [PBu$_4$]Br and said 2-BrPA have a molar ratio of about 9:1; wherein said acrylic acid of said second stream is combined with said acrylic acid of said third stream into a production stream of said acrylic acid; and wherein said acrylic acid in said production stream has an overall acrylic acid yield of about 55 mol % and an overall acrylic acid selectivity of about 83 mol %.

BRIEF DESCRIPTION OF THE DRAWINGS

For a more complete understanding of the disclosure, reference should be made to the following detailed description of the invention and drawing figures.

DETAILED DESCRIPTION OF THE INVENTION

I Definitions

Figure 1:
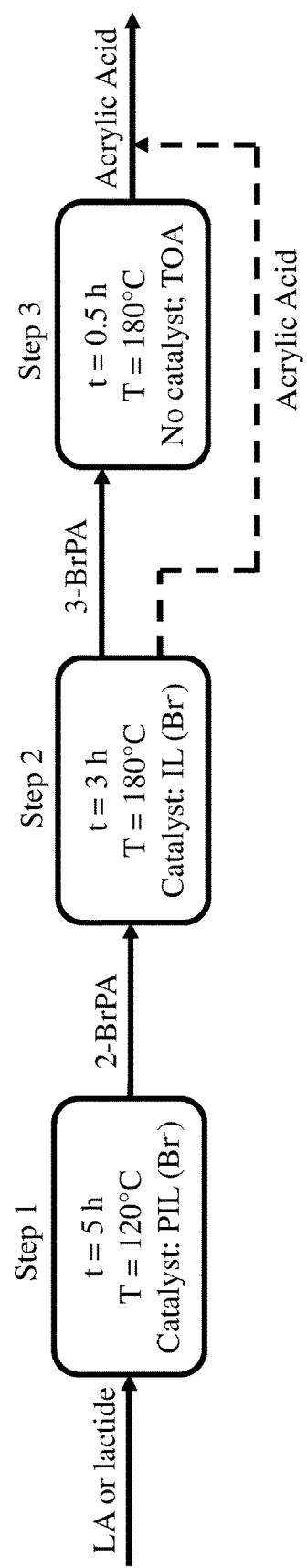
FIG. 1 illustrates one embodiment of the three-step method of making acrylic acid of the present invention.

As used herein, the term "fossil-derived" material refers to a material that is produced from fossil resources, such as crude oil (petroleum), natural gas, coal, peat, etc.

As used herein, the term "non-fossil-derived" material refers to a material that is produced from non-fossil resources. For clarity and for the purposes of the present invention, the terms "renewable" material, "bio-based" material, "non-petroleum" material, and "non-fossil-derived" material are used interchangeably.

As used herein, the term "renewable" material refers to a material that is produced from a renewable resource, which is a resource produced via a natural process at a rate comparable to its rate of consumption (e.g., within a 100 year time frame). The renewable resource can be replenished naturally or via agricultural techniques. Non-limiting examples of renewable resources include plants (such as sugar cane, beets, corn, potatoes, citrus fruit, woody plants, lignocellulose, hemicellulose, and cellulosic waste), animals, fish, bacteria, fungi, and forestry products. These resources can be naturally occurring, hybrids, or genetically engineered organisms. Fossil resources take longer than 100 years to form and thus they are not considered renewable resources.

As used herein, the term "renewable content" refers to the amount of carbon from a renewable resource in a material as a percent of the weight (mass) of the total organic carbon in the material, as determined by ASTM D6866-10 Method B.

As used herein, the term "chemically inert" material refers to a material which remains in the same chemical form, under equilibrium conditions, when contacted with another material or materials. In the context of the present invention, more than about 90 wt % of the material should remain in the same chemical form to be considered a "significantly chemically inert" material and more than about 98 wt % of the material should remain in the same chemical form to be considered an "essentially chemically inert" material.

As used herein, the term "strip gas" refers to a gas that is used to physically separate one or more components from a liquid stream. Typically a strip gas is made to interact with a liquid stream in either co-current or counter-current flows to allow volatile components in the liquid stream to partition into the strip gas and be carried away by the gas stream for subsequent collection.

As used herein, the term "better leaving group" refers to a chemical group attached to the α carbon position of lactic acid that can be removed easier (e.g. milder operating conditions, or lower activation energy, or faster removal rate, etc.) than the αcarbon hydroxyl group of lactic acid in a dehydration reaction. Better leaving groups are better able to stabilize the additional electron density that results from bond heterolysis than the hydroxide anion; i.e., better leaving groups exhibit lower Gibbs energies of activation ΔG‡'s for elimination than the ΔG‡ for elimination of the hydroxide anion. A list of better leaving groups than the hydroxyl group can be found in Table 10.10 of *J. March, Advanced Organic Chemistry*—Reactions, Mechanisms, and Structure, 4$^{th}$ Ed., Wiley 1992, with specific examples of better leaving groups being: —N$_2^+$, —OR$_2^+$, —OSO$_2$F, OSO$_2$CF$_3$, —I, —Br, —Cl, —F, —OH$_2^+$, —NH$_3^+$, and —OAr.

As used herein, the terms "LA" refers to lactic acid, "AA" refers to acrylic acid, "AcH" refers to acetaldehyde, and "PA" refers to propionic (also known as propanoic) acid.

As used herein, the term "lactide" refers to the cyclic di-ester of lactic acid, as it is well known to those skilled in the art.

As used herein, the term "lactic acid, lactide, or mixtures thereof" refers to lactic acid monomer and oligomers, lactide, and mixtures of lactic acid monomer and oligomers, and lactide.

As used herein, the term "lactic acid equivalent" refers to the lactic acid mols contained within lactic acid, lactide, or mixtures thereof. As such, the lactic acid equivalent of 1 mol of lactic acid is 1 mol, the lactic acid equivalent of 1 mol of lactide is 2 mols of lactic acid, and the lactic acid equivalent of 1 mol of a mixture of lactic acid and lactide depends on the mol fraction of lactic acid in the mixture.

As used herein, the term "conversion" in mol % is defined as [lactic acid, lactide, or mixtures thereof flow rate in (mol/min)−lactic acid, lactide, or mixtures thereof flow rate out (mol/min)]/[lactic acid, lactide, or mixtures thereof flow rate in (mol/min)]×100.

As used herein, the term "yield" in mol % is defined as [product flow rate out (mol/min)/lactic acid, lactide, or mixtures thereof flow rate in (mol/min)]×100.

As used herein, the term "overall yield" in mol % is defined as the yield of a chemical from the first step to the last step in the production process, i.e., from the feed stream to the overall process production stream.

As used herein, the term "selectivity" in mol % is defined as [Yield/Conversion]×100.

As used herein, the term "overall selectivity" in mol % is defined as the selectivity of a chemical from the first step to the last step in the production process, i.e., from the feed stream to the overall process production stream.

As used herein, the term "Weight Hourly Space Velocity" or "WHSV" in $h^{-1}$ is defined as 60×[Total lactic acid flow rate (g/min)/catalyst weight (g)]. For the purpose of this definition, the catalyst weight does not include the weight of any inert support.

As used herein, the term "ionic liquid" (IL) refers to a salt with a melting temperature below the boiling point of water. Typically, an IL is made of poorly-coordinated ions and short-lived ion pairs.

As used herein, the term "protic ionic liquid" (PIL) refers to an ionic liquid (IL) which includes a proton. Typically, a PIL is formed by a proton transfer between a Brønsted acid (AH) and a Brønsted base (B), and in this case the PIL is noted as $[BH^+][A^-]$.

Figure 2:
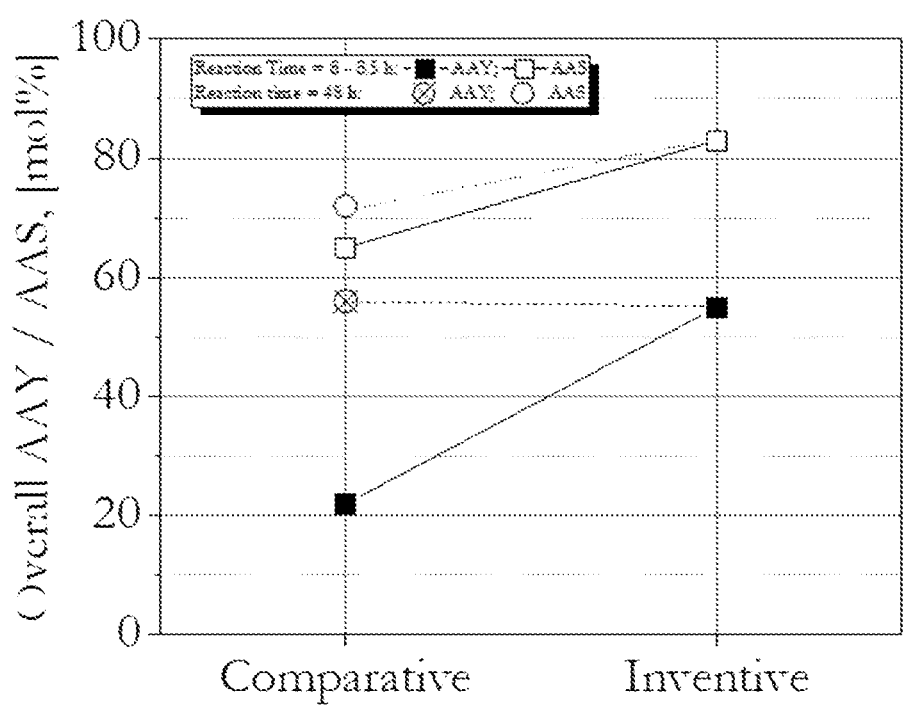
FIG. 2 illustrates the overall yield and overall selectivity of acrylic acid from one embodiment of the three-step method of the present invention with a total reaction time of 8.5 h, and a comparative embodiment of the one-step method with total reaction times of 8 h and 48 h.

II Catalysts for the Dehydration of Lactic Acid, Lactide, or Mixtures Thereof to Acrylic Acid Unexpectedly, it has been found that a three-step method (see FIG. 1 for an embodiment of the present invention) can convert lactic acid, lactide, or mixtures thereof in liquid phase to acrylic acid with yield and selectivity (i.e., low amount and few side products) with the use of two molten salt catalysts (one comprising a protic ionic liquid (PIL) and the other comprising an ionic liquid (IL); both including a bromide anion (Br)) and an amine via two intermediates, i.e., 2-BrPA and 3-BrPA. The acrylic acid yield and selectivity are unexpectedly much higher than those from a one-step method of converting lactic acid or lactic acid derivatives to acrylic acid. FIG. 2 shows the unexpected benefits of the present invention. More specifically, the overall acrylic acid yield and overall acrylic acid selectivity from one embodiment of the present invention (i.e., 55 mol % and 83 mol % at a total reaction time of 8.5 h, respectively; combination of Examples 13, 42, and 55) are much higher than those from a comparative embodiment of a one-step method (i.e., 22 mol % and 65 mol % at a reaction time of 8 h, respectively; 52 mol % and 72 mol % at a reaction time of 48 h, respectively; Comparative Example 2). In this particular case, the overall acrylic acid yield from the embodiment of the present invention is 2.5 times that from the comparative embodiment, and the overall acrylic acid selectivity from the embodiment of the present invention is 1.3 times that from the comparative embodiment, at the same overall reaction time of 8 h to 8.5 h.

For the purposes of the present invention, the term "molten salt catalyst" refers to a catalyst that comprises an IL, which is a salt in the liquid state. In some context, the term refers to salts with a melting temperature below the boiling point of water. Also, ILs are categorized in protic ILs (PILs) and aprotic ILs (AILs). While typical liquids are made of electrically neutral molecules, ILs are primarily made of poorly-coordinated ions and short-lived ion pairs. Other names for ILs found in the literature are "room temperature molten salts", "low temperature molten salts", "ambient temperature molten salt", "ionic melts", "ionic fluids", "fused salts", "ionic glasses", "liquid electrolytes", and "liquid organic salt". Non-limiting examples of ILs are 1-ethyl-3-methylimidazolium chloride, 1-butyl-3-methylimidazolium chloride, 1-ethyl-3-methylimidazolium methanesulfonate, 1-butyl-3-methylimidazolium methanesulfonate, methylimidazolium chloride, 1-ethyl-3-methylimidazolium acetate, 1-ethyl-3-methylimidazolium ethyl sulfate, 1-ethyl-3-methylimidazolium thiocyanate, 1-butyl-3-methylimidazolium hexafluorophosphate, 1-ethyl-3-methylimidazolium tetrafluoroborate, tetrabutylphosphonium bromide, tetrabutylammonium bromide, 1-butylpyridinium bromide, 1-butyl-1-methylpyrrolidinium chloride, and tetrahexylammonium iodide. Non limiting examples of PILs can be found in T. L. Greaves and C. J. Drummond, Chem. Rev. 2008, 108, 206-237.

As salts, ILs have an anion and a cation. In one embodiment of the present invention, said IL has an organic cation. In another embodiment of the present invention, said IL has an organic cation selected from the group consisting of imidazolium, pyridinium, pyrrolidinium, ammonium, phosphonium, their derivatives, and mixtures thereof. In yet another embodiment of the present invention, said IL has a phosphonium cation. In even yet another embodiment of the present invention, said phosphonium cation is selected from the group consisting of alkyl substituted phosphonium cations, aryl substituted phosphonium cations, mixed alkyl aryl substituted phosphonium cations, and mixtures thereof. Non-limiting examples of alkyl substituted phosphonium cations are tetrabutylphosphonium, tributylethylphosphonium, dibutyldiethylphosphonium, and butyltriethylphosphonium. Non-limiting examples of aryl substituted phosphonium cations are tetraphenylphosphonium, triphenyl-p-tolylphosphonium, diphenyl-di-p-tolylphosphonium, phenyl-tri-p-tolylphosphonium, and tetra-p-tolylphosphonium. Non-limiting examples of alkyl aryl substituted phosphonium cations are ethyltriphenylphosphonium, diethydiphenylphosphonium, triethylphenylphosphonium, tributylphenylphosphonium, and tributyl-p-tolylphosphonium. In one embodiment of the present invention, said IL has a tetrabutylphosphonium cation. In another embodiment of the present invention, said IL has an ethyltriphenylphosphonium cation. In another embodiment of the present invention, said IL has an organic anion. In yet another embodiment of the present invention, said organic anion is selected from the group consisting of alkylsulfate, tosylate, methanesulfonate, and mixtures thereof. In one embodiment of the present invention, said IL has an inorganic anion. In another embodiment of the present invention, said inorganic anion is selected from the group consisting of chloride ($Cl^-$), bromide ($Br®$), iodide ($I^-$), tetrafluoroborate ($BF_4^-$), hexafluorophosphate ($PF_6^-$), bis(trifluoromethylsulfonyl) amide, and mixtures thereof. In yet another embodiment of the present invention, said inorganic anion is bromide ($Br^-$).

In one embodiment of the present invention, the first molten salt catalyst comprises a protic ionic liquid (PIL). In another embodiment of the present invention, said PIL comprises a bromide anion ($Br^-$). In yet another embodiment of the present invention, said PIL comprises 3-methyl-1-(4-butane sulfonic acid) imidazolium bromide ([MIMBS]Br).

In one embodiment of the present invention, the second molten salt catalyst comprises an ionic liquid (IL). In another embodiment of the present invention, said IL comprises a bromide anion ($Br^-$). In yet another embodiment of the present invention, said IL comprises tetrabutylphosphonium bromide ($[PBu_4]Br$). In even another embodiment of the present invention, said IL is ethyltriphenylphosphonium bromide ($EtPPh_3Br$). In one embodiment of the present invention, said IL is selected from the group consisting of 1-ethyl-3-methylimidazolium bromide ([EMIM]Br), 1-butyl-4-methylpyridinium bromide ([1B4MPyr]Br), 1-ethyl-1-methylpyrrolidinium bromide ([1E1MPyrro]Br), ethyl triphenylphosphonium bromide ($[PPh_3Et]Br$), butyltriphenylphosphonium bromide ($[PBuPh_3]Br$), butyltriphenylphosphonium bromide ($[PBuPh_3]Br$), tributylphenylphosphonium bromide ($[PBu_3Ph]Br$), and mixtures thereof.

In one embodiment of the present invention, the first molten salt catalyst comprising a PIL further comprises other compound which is significantly chemically inert to said PIL. In another embodiment of the present invention, the second molten salt catalyst comprising an IL further comprises other compound which is significantly chemically inert to said IL. In yet another embodiment of the present invention, said other compound comprises a cation and an anion. Non-limiting examples of anions in the other compound are arsenates, condensed arsenates, nitrates, sulfates, condensed sulfates, borates, carbonates, chromates, condensed chromates, vanadates, niobates, tantalates, selenates, condensed silicates, condensed aluminates, germanates, condensed germanates, molybdates, condensed molybdates, other monomeric oxyanions, polyoxyanions, heteropolyphosphates, such as arsenatophosphates, phosphoaluminates, phosphoborates, phosphochromates, phosphomolybdates, phosphosilicates, phosphosulfates, phosphotungstates, and phosphate adducts, such as phosphate anions with telluric acid, halides, borates, carbonates, nitrates, sulfates, chromates, silicates, oxalates, mixtures thereof, or others that may be apparent to those having ordinary skill in the art.

In one embodiment of the present invention, said first molten salt catalyst further comprises an inert support. In another embodiment of the present invention, said second molten salt catalyst further comprises an inert support. Non-limiting examples of inert supports are silica, silicate, alumina, aluminate, aluminosilicate, titania, titanate, zirconia, zirconate, carbon (such as activated carbon, diamond, graphite, or fullerenes), sulfate, phosphate, tantalate, ceria, other metal oxides, and mixtures thereof. In yet another embodiment of the present invention, said inert support consists essentially of silica. In even yet another embodiment of the present invention, said silica is selected from the group consisting of amorphous silica, quartz, tridymite, cristobalite, moganite, coesite, and mixtures thereof. In one embodiment of the present invention, said silica is amorphous silica. In another embodiment of the present invention, said silica has a specific surface area of less than about 10 $m^2/g$. In yet another embodiment of the present invention, the inert support represents an amount between about 20 wt % and about 90 wt %, based on the total weight of the active catalyst.

In one embodiment of the present invention, the weight of the PIL based on the total weight of the first molten salt catalyst is about 100 wt %. In another embodiment of the present invention, the weight of the PIL based on the total weight of the first molten salt catalyst is between about 5 wt % and about 90 wt %. In yet another embodiment of the present invention, the weight of the PIL based on the total weight of the first molten salt catalyst is between about 20 wt % and about 80 wt %. In even yet another embodiment of the present invention, the weight of the PIL based on the total weight of the first molten salt catalyst is between about 40 wt % and about 60 wt %. In one embodiment of the present invention, the weight of the PIL based on the total weight of the first molten salt catalyst is about 50 wt %.

In one embodiment of the present invention, the weight of the IL based on the total weight of the second molten salt catalyst is about 100 wt %. In another embodiment of the present invention, the weight of the IL based on the total weight of the second molten salt catalyst is between about 5 wt % and about 90 wt %. In yet another embodiment of the present invention, the weight of the IL based on the total weight of the second molten salt catalyst is between about 20 wt % and about 80 wt %. In even yet another embodiment of the present invention, the weight of the IL based on the total weight of the second molten salt catalyst is between about 40 wt % and about 60 wt %. In one embodiment of the present invention, the weight of the IL based on the total weight of the second molten salt catalyst is about 50 wt %.

Besides a PIL, the first molten salt catalyst of the present invention can include a phosphine oxide $OPX_3$, where X can be selected from a variety of groups. Besides an IL, the second molten salt catalyst of the present invention can include a phosphine oxide $OPX_3$, where X can be selected from a variety of groups. Non-limiting examples of phosphine oxides are triphenylphosphine oxide (TPPO), tributylphosphine oxide (TBPO), triethylphosphine oxide (TEPO), and trioctylphosphine oxide (TOPO).

The molten salt catalysts of the present invention can be utilized to catalyze several chemical reactions. Non-limiting examples of reactions are: dehydration of lactic acid, lactic acid derivatives, or mixtures thereof to acrylic acid; dehydration of 3-hydroxypropionic acid, 3-hydroxypropionic acid derivatives, or mixtures thereof to acrylic acid; dehydration of glycerin to acrolein; isomerization of lactic acid to 3-hydroxypropionic acid in the presence of water; reduction of hydroxypropionic acid to propionic acid or 1-propanol in the presence of hydrogen gas; dehydration of aliphatic alcohols to alkenes or olefins; dehydrogenation of aliphatic alcohols to ethers; other dehydrogenations, hydrolyses, alkylations, dealkylations, oxidations, disproportionations, esterifications, cyclizations, isomerizations, condensations, aromatizations, polymerizations; and other reactions that may be apparent to those having ordinary skill in the art.

III Methods of Making Acrylic Acid from Lactic Acid, Lactide, or Mixtures Thereof A method of dehydrating lactic acid, lactide, or mixtures thereof to acrylic acid is provided. The method comprises the steps: (a) contacting a feed stream comprising lactic acid, lactide, or mixtures thereof with a first molten salt catalyst in a first reactor at a first reaction temperature and a first reaction time to produce a first stream comprising 2-bromopropionic acid (2-BrPA); (b) contacting said 2-BrPA with a second molten salt catalyst in a second reactor at a second reaction temperature and a second reaction time to produce a second stream comprising 3-bromopropionic acid (3-BrPA) and said acrylic acid; and (c) contacting said 3-BrPA with an amine in a third reactor at a third reaction temperature and a third reaction time to produce a third stream comprising said acrylic acid; wherein said first molten salt catalyst comprises a bromide anion (Br$^-$); wherein said second molten salt catalyst comprises a Br$^-$; wherein said acrylic acid of said second stream is combined with said acrylic acid of said third stream into a production stream of said acrylic acid; and wherein said acrylic acid in said production stream has an overall acrylic acid yield and an overall acrylic acid selectivity. FIG. 1 shows a schematic of an embodiment of the present invention.

Lactic acid can be D-lactic acid, L-lactic acid, or mixtures thereof (including racemic mixture), and lactide is the cyclic di-ester of lactic acid. It is well known to those skilled in the art that the αcarbon hydroxyl group of lactic acid is not a good leaving group and that the carboxylic group of lactic acid is prone to decarboxylation or decarbonylation. This decarboxylation and decarbonylation is easier than the removal of the hydroxyl group, and that is the reason that many past attempts failed to produce commercially-viable quantities of acrylic acid. Although not wishing to be bound by any theory, applicants believe that commercially-viable quantities of acrylic acid can be produced from lactic acid if the hydroxyl group is replaced by a better leaving group, the carboxylic group is protected, or both the hydroxyl group is replaced by a better leaving group and the carboxylic group is protected. A preferred better leaving group for the purposes of the present invention is Br$^-$.

Lactic acid can be in monomeric form or as oligomers in said feed stream. In one embodiment of the present invention, the oligomers of the lactic acid in said feed stream are less than about 30 wt % based on the total amount of lactic acid, lactide, or mixtures thereof. In another embodiment of the present invention, the oligomers of the lactic acid in said feed stream are less than about 10 wt % based on the total amount of lactic acid, lactide, or mixtures thereof. In yet another embodiment of the present invention, the oligomers of the lactic acid feed stream are less than about 5 wt % based on the total amount of lactic acid, lactide, or mixtures thereof. In even yet another embodiment of the present invention, the lactic acid is essentially in monomeric form in said feed stream.

The process to remove the oligomers from the feed stream can comprise a purification step or hydrolysis by heating step. In one embodiment of the present invention, the heating step can involve heating the feed stream at a temperature between about 50° C. and about 100° C. to hydrolyze the oligomers of the lactic acid. In another embodiment of the present invention, the heating step can involve heating the feed stream at a temperature between about 95° C. and about 100° C. to hydrolyze the oligomers of the lactic acid. In yet another embodiment of the present invention, the heating step can involve heating the feed stream at a temperature between about 50° C. and about 100° C. to hydrolyze the oligomers of the lactic acid and produce a monomeric lactic acid feed stream comprising at least 80 wt % of lactic acid in monomeric form based on the total amount of lactic acid, lactide, or mixtures thereof. In even yet another embodiment of the present invention, the heating step can involve heating the feed stream at a temperature between about 50° C. and about 100° C. to hydrolyze the oligomers of the lactic acid and produce a monomeric lactic acid feed stream comprising at least 95 wt % of lactic acid in monomeric form based on the total amount of lactic acid, lactide, or mixtures thereof. In one embodiment of the present invention, an about 88 wt % aqueous solution of lactic acid, lactide, or mixtures thereof is diluted with water and the oligomers are hydrolyzed to produce an aqueous solution of about 20 wt % lactic acid.

Lactic acid can be produced by sugar fermentation or chemical conversion of sugars or other feedstock materials, such as glycerin. Nearly all world production of lactic acid is by sugar fermentation today; however, there are chemical conversion technologies currently in pilot or demo scale. Also, the sugar feedstock can be generation 1 sugar (i.e., sugar from corn, sugarcane, sugar beets, wheat, potato, rice, etc.) or generation 2 sugar (i.e., sugar from the hydrolysis of biomass or agricultural waste, such as bagasse, corn stover, rice husk, wheat straw, etc.).

In one embodiment of the present invention, the feed stream comprises a liquid. In another embodiment of the present invention, the feed stream comprises a solid. In yet another embodiment of the present invention, the feed stream comprises a liquid and a solid. In even yet another embodiment of the present invention, the feed stream comprises a liquid and a gas.

In one embodiment of the present invention, said feed stream further comprises an essentially chemically inert diluent. In the context of the present invention, an essentially chemically inert diluent is any diluent that is essentially chemically inert to said lactic acid, lactide, or mixtures thereof, but not necessarily to said first molten salt catalyst. Non-limiting examples of essentially chemically inert diluents are water, hydrocarbons, chlorinated hydrocarbons, brominated hydrocarbons, fluorinated hydrocarbons, esters, ethers, ketones, and mixtures thereof. Non-limiting examples of hydrocarbons are C5 to C8 linear and branched alkanes. A non-limiting example of esters is ethyl acetate. A non-limiting example of ethers is diphenyl ether. A non-limiting example of ketones is acetone. In another embodiment of the present invention, said essentially chemically inert diluent comprises water. In yet another embodiment of the present invention, said essentially chemically inert diluent consists essentially of water. In even yet another embodiment of the present invention said feed stream consists essentially of lactic acid, lactide, or mixtures thereof.

In one embodiment of the present invention, the feed stream comprising lactic acid, lactide, or mixtures thereof can further comprise one or more antioxidants. In another embodiment of the present invention, the feed stream comprising lactic acid, lactide, or mixtures thereof further comprises butylated hydroxy toluene (BHT), butylated hydroxy anisole (BHA), or mixtures thereof. In yet another embodiment of the present invention, the feed stream comprising lactic acid, lactide, or mixtures thereof further comprises ethylene glycol, ethanedithiol, methanol, methanethiol, or mixtures thereof.

In one embodiment of the present invention, the concentration of the lactic acid, lactide, or mixtures thereof in said feed stream is between about 1 wt % and about 100 wt %. In another embodiment of the present invention, the concentration of the lactic acid, lactide, or mixtures thereof in said feed stream is between about 5 wt % and about 95 wt %. In yet another embodiment of the present invention, the concentration of the lactic acid, lactide, or mixtures thereof in said feed stream is between about 20 wt % and about 80 wt %. In even yet another embodiment of the present invention, the concentration of the lactic acid, lactide, or mixtures thereof in said feed stream is about 25 wt %. In one embodiment of the present invention, the concentration of the lactic, lactide, or mixtures thereof in said feed stream is about 50 wt %. In another embodiment of the present invention, the feed stream consists essentially of lactide.

Non-limiting examples of reactors suitable for use in the present invention are static reactors, stirred tank reactors, recirculation reactors, trickle bed reactors, and combinations thereof. In one embodiment of the present invention, the reactor is a stirred tank reactor. In another embodiment of the present invention, the stirred tank reactor is a single-layer reactor. A single-layer reactor consists of a single layer (also called wall) that extends from the inner surface to the outer surface and has a wall thickness. The inner surface is in contact with the molten salt catalyst, the feed stream, and the product stream. In one embodiment of the present invention, the single-layer reactor comprises a wall, an outer surface, and an inner surface; wherein said wall is made from a wall material, has a wall thickness, and extends from said outer surface to said inner surface; and wherein said inner surface is in contact with said molten salt catalyst, feed stream, and product stream.

In one embodiment of the present invention, the wall thickness of a single-layer reactor is between about 2 mm and about 30 mm. In another embodiment of the present invention, the wall thickness of a single-layer reactor is between about 3 mm and about 20 mm. In yet another embodiment of the present invention, the wall thickness of a single-layer reactor is between about 4 mm and about 10 mm. In even yet another embodiment of the present invention, the wall thickness of a single-layer reactor is between about 5 mm and about 8 mm.

In one embodiment of the present invention, the stirred tank reactor is a bi-layer reactor. The bi-layer reactor comprises an inner surface, which is in contact with the molten salt catalyst, feed stream, and product stream, and is the innermost surface of the bi-layer reactor. The bi-layer reactor consists of an inner layer, which has an inner layer thickness, an outer layer, which has an outer layer thickness, an interface between the outer layer and the inner layer, and an outer surface, which is the outmost surface of the bi-layer reactor. In another embodiment of the present invention, the outer layer of the bi-layer reactor consists of two or more sublayers. In yet another embodiment of the present invention, the bi-layer reactor comprises an outer layer, an inner layer, an outer surface, an inner surface, and an interface between said outer layer and said inner layer; wherein said outer layer is made from an outer layer material, has an outer layer thickness, and extends from said interface to said outer surface; wherein said inner layer is made from an inner layer material, has an inner layer thickness, and extends from said inner surface to said interface; and wherein said inner surface is in contact with said molten salt catalyst, feed stream, and product stream. In even yet another embodiment of the present invention, said outer layer comprises two or more sublayers.

In one embodiment of the present invention, the inner layer thickness of a bi-layer reactor is between about 1 mm and about 20 mm. In another embodiment of the present invention, the inner layer thickness of a bi-layer reactor is between about 1.5 mm and about 10 mm. In yet another embodiment of the present invention, the inner layer thickness of a bi-layer reactor is between about 2 mm and about 8 mm. In even yet another embodiment of the present invention, the inner layer thickness of a bi-layer reactor is between about 3 mm and about 6 mm. In one embodiment of the present invention, the outer layer thickness of a bi-layer reactor is between about 1 mm and about 20 mm. In another embodiment of the present invention, the outer layer thickness of a bi-layer reactor is between about 1.5 mm and about 10 mm. In yet another embodiment of the present invention, the outer layer thickness of a bi-layer reactor is between about 2 mm and about 8 mm. In even yet another embodiment of the present invention, the outer layer thickness of a bi-layer reactor is between about 3 mm and about 6 mm.

The molten salt catalysts, or the feed stream, or the product stream of the present invention can be corrosive to the reactors. Non-limiting examples of materials that can be used in the present invention as either wall materials or inner layer materials are glass; silica; sapphire; titanium; copper; silver; gold; tungsten; tantalum; zirconium; HASTELLOY® and HAYNES® alloys (Ni-based alloys; Haynes International, Inc.; Kokomo, Ind.); INCONEL®, INCOLOY®, and MONEL® alloys (Ni-based alloys; Special Metals Corporation; Huntington, W. Va.); and plastic materials (e.g., polytetrafluoroethylene (PTFE), polyetherether ketone (PEEK), and polyether sulfone (PES)). In one embodiment of the present invention, the outer layer material is selected from the group consisting of stainless steel and carbon steel. In another embodiment of the present invention, the outer layer material is stainless steel and the inner layer material of the bi-layer reactor is titanium.

In one embodiment of the present invention, the single-layer reactor has a corrosion rate lower than about 1.3 mm/y. In another embodiment of the present invention, the bi-layer reactor has a corrosion rate lower than about 1.3 mm/y. For the purposes of the present invention, the corrosion rate is measured by weighing a wall material sample or an inner layer material sample before and after exposure to the reaction conditions, as this is known to those skilled in the art.

In one embodiment of the present invention, said corrosion rate is lower than about 1 mm/y. In another embodiment of the present invention, said corrosion rate is lower than about 0.5 mm/y. In yet another embodiment of the present invention, said corrosion rate is lower than about 0.13 mm/y. In even yet another embodiment of the present invention, said corrosion rate is lower than about 0.05 mm/y.

In one embodiment of the present invention, the first molten salt catalyst has a molar ratio to the lactic acid, lactide, or mixtures thereof of the feed stream between about 10:1 and about 1:1. In another embodiment of the present invention, the first molten salt catalyst has a molar ratio to the lactic acid, lactide, or mixtures thereof of the feed stream between about 8:1 and about 2:1. In yet another embodiment of the present invention, the first molten salt catalyst has a molar ratio to the lactic acid, lactide, or mixtures thereof of the feed stream between about 6:1 and about 3:1. In even yet another embodiment of the present invention, the first molten salt catalyst has a molar ratio to the lactic acid, lactide, or mixtures thereof of the feed stream of about 6:1. In one embodiment of the present invention, the first molten salt catalyst has a molar ratio to the lactic acid, lactide, or mixtures thereof of the feed stream of about 3:1.

In one embodiment of the present invention, the PIL of the first molten salt catalyst has a molar ratio to the lactic acid, lactide, or mixtures thereof of the feed stream between about 10:1 and about 1:1. In another embodiment of the present invention, the PIL of the first molten salt catalyst has a molar ratio to the lactic acid, lactide, or mixtures thereof of the feed stream between about 8:1 and about 2:1. In yet another embodiment of the present invention, the PIL of the first molten salt catalyst has a molar ratio to the lactic acid, lactide, or mixtures thereof of the feed stream between about 6:1 and about 3:1. In even yet another embodiment of the present invention, the PIL of the first molten salt catalyst has a molar ratio to the lactic acid, lactide, or mixtures thereof of the feed stream of about 6:1. In one embodiment of the present invention, the PIL of the first molten salt catalyst has a molar ratio to the lactic acid, lactide, or mixtures thereof of the feed stream of about 3:1.

In one embodiment of the present invention, the [MIMBS]Br of the first molten salt catalyst has a molar ratio to the lactic acid, lactide, or mixtures thereof of the feed stream between about 10:1 and about 1:1. In another embodiment of the present invention, the [MIMBS]Br of the first molten salt catalyst has a molar ratio to the lactic acid, lactide, or mixtures thereof of the feed stream between about 8:1 and about 2:1. In yet another embodiment of the present invention, the [MIMBS]Br of the first molten salt catalyst has a molar ratio to the lactic acid, lactide, or mixtures thereof of the feed stream between about 6:1 and about 3:1. In even yet another embodiment of the present invention, the [MIMBS]Br of the first molten salt catalyst has a molar ratio to the lactic acid, lactide, or mixtures thereof of the feed stream of about 6:1. In one embodiment of the present invention, the [MIMBS]Br of the first molten salt catalyst has a molar ratio to the lactic acid, lactide, or mixtures thereof of the feed stream of about 3:1.

In one embodiment of the present invention, the first molten salt catalyst further comprises a dilute HBr aqueous solution. In another embodiment of the present invention, the dilute HBr aqueous solution comprises 20 mmol HBr.

In one embodiment of the present invention, the second molten salt catalyst has a molar ratio to the 2-BrPA in the second reactor between about 30:1 and about 1:2. In another embodiment of the present invention, the second molten salt catalyst has a molar ratio to the 2-BrPA in the second reactor between about 20:1 and about 2:3. In yet another embodiment of the present invention, the second molten salt catalyst has a molar ratio to the 2-BrPA in the second reactor between about 10:1 and about 2:1. In even yet another embodiment of the present invention, the second molten salt catalyst has a molar ratio to the 2-BrPA in the second reactor of about 9:1. In one embodiment of the present invention, the second molten salt catalyst has a molar ratio to the 2-BrPA in the second reactor of about 3:1. In another embodiment of the present invention, the second molten salt catalyst has a molar ratio to the 2-BrPA in the second reactor of about 6:1. In yet another embodiment of the present invention, the second molten salt catalyst has a molar ratio to the 2-BrPA in the second reactor of about 18:1. In even yet another embodiment of the present invention, the second molten salt catalyst has a molar ratio to the 2-BrPA in the second reactor of about 1:1.

In one embodiment of the present invention, the IL of the second molten salt catalyst has a molar ratio to the 2-BrPA in the second reactor between about 30:1 and about 1:2. In another embodiment of the present invention, the IL of the second molten salt catalyst has a molar ratio to the 2-BrPA in the second reactor between about 20:1 and about 2:3. In yet another embodiment of the present invention, the IL of the second molten salt catalyst has a molar ratio to the 2-BrPA in the second reactor between about 10:1 and about 2:1. In even yet another embodiment of the present invention, the IL of the second molten salt catalyst has a molar ratio to the 2-BrPA in the second reactor of about 9:1. In one embodiment of the present invention, the IL of the second molten salt catalyst has a molar ratio to the 2-BrPA in the second reactor of about 3:1. In another embodiment of the present invention, the IL of the second molten salt catalyst has a molar ratio to the 2-BrPA in the second reactor of about 6:1. In yet another embodiment of the present invention, the IL of the second molten salt catalyst has a molar ratio to the 2-BrPA in the second reactor of about 18:1. In even yet another embodiment of the present invention, the IL of the second molten salt catalyst has a molar ratio to the 2-BrPA in the second reactor of about 1:1.

In one embodiment of the present invention, the [PBu$_4$]Br of the second molten salt catalyst has a molar ratio to the 2-BrPA in the second reactor between about 30:1 and about 1:2. In another embodiment of the present invention, the [PBu$_4$]Br of the second molten salt catalyst has a molar ratio to the 2-BrPA in the second reactor between about 20:1 and about 2:3. In yet another embodiment of the present invention, the [PBu$_4$]Br of the second molten salt catalyst has a molar ratio to the 2-BrPA in the second reactor between about 10:1 and about 2:1. In even yet another embodiment of the present invention, the [PBu$_4$]Br of the second molten salt catalyst has a molar ratio to the 2-BrPA in the second reactor of about 9:1. In one embodiment of the present invention, the [PBu$_4$]Br of the second molten salt catalyst has a molar ratio to the 2-BrPA in the second reactor of about 3:1. In another embodiment of the present invention, the [PBu$_4$]Br of the second molten salt catalyst has a molar ratio to the 2-BrPA in the second reactor of about 6:1. In yet another embodiment of the present invention, the [PBu$_4$]Br of the second molten salt catalyst has a molar ratio to the 2-BrPA in the second reactor of about 18:1. In even yet another embodiment of the present invention, the [PBu$_4$]Br of the second molten salt catalyst has a molar ratio to the 2-BrPA in the second reactor of about 1:1.

In one embodiment of the present invention, the [EMIM]Br of the second molten salt catalyst has a molar ratio to the 2-BrPA in the second reactor between about 30:1 and about 1:2. In another embodiment of the present invention, the [EMIM]Br of the second molten salt catalyst has a molar ratio to the 2-BrPA in the second reactor between about 20:1 and about 2:3. In yet another embodiment of the present invention, the [EMIM]Br of the second molten salt catalyst has a molar ratio to the 2-BrPA in the second reactor between about 10:1 and about 2:1. In even yet another embodiment of the present invention, the [EMIM]Br of the second molten salt catalyst has a molar ratio to the 2-BrPA in the second reactor of about 9:1. In one embodiment of the present invention, the [EMIM]Br of the second molten salt catalyst has a molar ratio to the 2-BrPA in the second reactor of about 3:1. In another embodiment of the present invention, the [EMIM]Br of the second molten salt catalyst has a molar ratio to the 2-BrPA in the second reactor of about 6:1. In yet another embodiment of the present invention, the [EMIM]Br of the second molten salt catalyst has a molar ratio to the 2-BrPA in the second reactor of about 18:1. In even yet another embodiment of the present invention, the [EMIM]Br of the second molten salt catalyst has a molar ratio to the 2-BrPA in the second reactor of about 1:1.

In one embodiment of the present invention, the first reaction temperature ranges from about 80° C. to about 160° C. In another embodiment of the present invention, the first reaction temperature ranges from about 100° C. and about 140° C. In yet another embodiment of the present invention, the first reaction temperature ranges from about 100° C. to about 120° C. In even yet another embodiment of the present invention, the first reaction temperature is about 120° C.

In one embodiment of the present invention, the second reaction temperature ranges from about 80° C. to about 200° C. In another embodiment of the present invention, the second reaction temperature ranges from about 100° C. and about 180° C. In yet another embodiment of the present invention, the second reaction temperature ranges from about 140° C. to about 180° C. In even yet another embodiment of the present invention, the second reaction temperature is about 160° C. In one embodiment of the present invention, the second reaction temperature is about 180° C.

In one embodiment of the present invention, the third reaction temperature ranges from about 50° C. to about 250° C. In another embodiment of the present invention, the third reaction temperature ranges from about 60° C. and about 200° C. In yet another embodiment of the present invention, the third reaction temperature ranges from about 80° C. to about 180° C. In even yet another embodiment of the present invention, the third reaction temperature is about 80° C. In one embodiment of the present invention, the third reaction temperature is about 180° C.

In one embodiment of the present invention, the first reaction time ranges from about 2 h to about 10 h. In another embodiment of the present invention, the first reaction time ranges from about 3 h and about 8 h. In yet another embodiment of the present invention, the first reaction time is about 5 h.

In one embodiment of the present invention, the second reaction time ranges from about 1 h to about 48 h. In another embodiment of the present invention, the second reaction time ranges from about 2 h and about 24 h. In yet another embodiment of the present invention, the second reaction time ranges from about 3 h and about 20 h. In even yet another embodiment of the present invention, the second reaction time is about 20 h. In one embodiment of the present invention, the second reaction time is about 3 h. In another embodiment of the present invention, the second reaction time is about 6 h.

In one embodiment of the present invention, the third reaction time ranges from about 0.25 h to about 5 h. In another embodiment of the present invention, the third reaction time ranges from about 0.4 h and about 2 h. In yet another embodiment of the present invention, the third reaction time is about 0.5 h. In even yet another embodiment of the present invention, the third reaction time is about 1 h.

The contacting of the feed stream and the first molten salt catalyst can be performed under vacuum, at atmospheric pressure, or at pressure higher than atmospheric. In one embodiment of the present invention, the contacting of the feed stream and the first molten salt catalyst is performed under a total pressure of at least about 1 bar. In another embodiment of the present invention, the contacting of the feed stream and the first molten salt catalyst is performed under a total pressure between about 250 mbar and about 2 bar. In yet another embodiment of the present invention, the contacting of the feed stream and the first molten salt catalyst is performed at atmospheric pressure.

In one embodiment of the present invention, the contacting of the feed stream and the first molten salt catalyst is performed with a WHSV between about 0.02 h$^{-1}$ and about 10 h$^{-1}$. In another embodiment of the present invention, the contacting of the feed stream and the first molten salt catalyst is performed with a WHSV between about 0.2 h$^{-1}$ and about 2 h$^{-1}$. In yet another embodiment of the present invention, the contacting of the feed stream and the first molten salt catalyst is performed with a WHSV between about 0.3 h$^{-1}$ and about 1.4 h$^{-1}$. In even yet another embodiment of the present invention, the contacting of the feed stream and the first molten salt catalyst is performed with a WHSV between about 0.3 h$^{-1}$ and about 0.4 h$^{-1}$. In one embodiment of the present invention, the contacting of the feed stream and the first molten salt catalyst is performed with a WHSV about 0.4 h$^{-1}$.

In one embodiment of the present invention, the 2-BrPA is produced in the first reactor at a yield of more than about 20 mol %. In another embodiment of the present invention, the 2-BrPA is produced in the first reactor at a yield of more than about 30 mol %. In yet another embodiment of the present invention, the 2-BrPA is produced in the first reactor at a yield of more than about 45 mol %. In even yet another embodiment of the present invention, the 2-BrPA is produced in the first reactor at a yield of more than about 70 mol %. In one embodiment of the present invention, the 2-BrPA is produced in the first reactor at a yield of about 60 mol %.

In one embodiment of the present invention, the 2-BrPA is produced in the first reactor with a selectivity of more than about 60 mol %. In another embodiment of the present invention, the 2-BrPA is produced in the first reactor with a selectivity of more than about 80 mol %. In yet another embodiment of the present invention, the 2-BrPA is produced in the first reactor with a selectivity of more than about 90 mol %. In even yet another embodiment of the present invention, the 2-BrPA is produced in the first reactor with a selectivity of more than about 92 mol %. In one embodiment of the present invention, the 2-BrPA is produced in the first reactor with a selectivity of more than about 95 mol %.

In one embodiment of the present invention, the 2-BrPA is produced in the first reactor at a yield of more than about 30 mol % and with a selectivity of more than about 90 mol %. In another embodiment of the present invention, the 2-BrPA is produced in the first reactor at a yield of more than about 45 mol % and with a selectivity of more than about 92 mol %. In yet another embodiment of the present invention, the 2-BrPA is produced in the first reactor at a yield of about 60 mol % and with a selectivity of more than about 95 mol %.

In one embodiment of the present invention, the 3-BrPA is produced in the second reactor at a yield of more than about 20 mol %. In another embodiment of the present invention, the 3-BrPA is produced in the second reactor at a yield of more than about 30 mol %. In yet another embodiment of the present invention, the 3-BrPA is produced in the second reactor at a yield of more than about 45 mol %. In even yet another embodiment of the present invention, the 3-BrPA is produced in the second reactor at a yield of more than about 70 mol %. In one embodiment of the present invention, the 3-BrPA is produced in the second reactor at a yield of about 79 mol %.

In one embodiment of the present invention, the 3-BrPA is produced in the second reactor with a selectivity of more than about 60 mol %. In another embodiment of the present invention, the 3-BrPA is produced in the second reactor with a selectivity of more than about 80 mol %. In yet another embodiment of the present invention, the 3-BrPA is produced in the second reactor with a selectivity of more than about 90 mol %. In even yet another embodiment of the present invention, the 3-BrPA is produced in the second reactor with a selectivity of more than about 92 mol %. In one embodiment of the present invention, the 3-BrPA is produced in the second reactor with a selectivity of about 89 mol %.

In one embodiment of the present invention, the 3-BrPA is produced in the second reactor at a yield of more than about 30 mol % and with a selectivity of more than about 90 mol %. In another embodiment of the present invention, the 3-BrPA is produced in the second reactor at a yield of more than about 45 mol % and with a selectivity of more than about 92 mol %. In yet another embodiment of the present invention, the 3-BrPA is produced in the second reactor at a yield of about 79 mol % and with a selectivity of about 89 mol %.

In one embodiment of the present invention, the 3-BrPA and the acrylic acid are produced in the second reactor at a combined yield of more than about 30 mol %. In another embodiment of the present invention, the 3-BrPA and the acrylic acid are produced in the second reactor at a combined yield of more than about 60 mol %. In yet another embodiment of the present invention, the 3-BrPA and the acrylic acid are produced in the second reactor at a combined yield of more than about 70 mol %. In even yet another embodiment of the present invention, the 3-BrPA and the acrylic acid are produced in the second reactor at a combined yield of more than about 80 mol %. In one embodiment of the present invention, the 3-BrPA and the acrylic acid are produced in the second reactor at a combined yield of more than about 95 mol %.

In one embodiment of the present invention, the amine in the third reactor is trioctylamine (TOA).

In one embodiment of the present invention, the acrylic acid is produced in the third reactor at a yield of more than about 60 mol %. In another embodiment of the present invention, the acrylic acid is produced in the third reactor at a yield of more than about 80 mol %. In yet another embodiment of the present invention, the acrylic acid is produced in the third reactor at a yield of more than about 90 mol %. In even yet another embodiment of the present invention, the acrylic acid is produced in the third reactor at a yield of about 90 mol %. In one embodiment of the present invention, the acrylic acid is produced in the third reactor at a yield of about 96 mol %.

In one embodiment of the present invention, the acrylic acid is produced in the third reactor with a selectivity of more than about 60 mol %. In another embodiment of the present invention, the acrylic acid is produced in the third reactor with a selectivity of more than about 80 mol %. In yet another embodiment of the present invention, the acrylic acid is produced in the third reactor with a selectivity of more than about 90 mol %.

In one embodiment of the present invention, the acrylic acid is produced in the third reactor at a yield of more than about 60 mol % and with a selectivity of more than about 80 mol %. In another embodiment of the present invention, the acrylic acid is produced in the third reactor at a yield of more than about 80 mol % and with a selectivity of more than about 90 mol %. In yet another embodiment of the present invention, the acrylic acid is produced in the third reactor at a yield of about 90 mol % and with a selectivity of more than about 90 mol %.

In one embodiment of the present invention, the overall acrylic acid yield is more than about 40 mol % and the overall acrylic acid selectivity is more than about 70 mol %. In another embodiment of the present invention, the overall acrylic acid yield is more than about 60 mol % and the overall acrylic acid selectivity is more than about 90 mol %. In yet another embodiment of the present invention, the overall acrylic acid yield is about 43 mol % and the overall acrylic acid selectivity is about 76 mol %. In even yet another embodiment of the present invention, the overall acrylic acid yield is about 55 mol % and the overall acrylic acid selectivity is about 83 mol %.

In one embodiment of the present invention, propionic acid is produced as an impurity along with said acrylic acid, wherein the selectivity of said propionic acid is less than about 5 mol %. In another embodiment of the present invention, propionic acid is produced as an impurity along with said acrylic acid, wherein the selectivity of said propionic acid is less than about 1 mol %.

In one embodiment of the present invention, the overall conversion of lactic acid, lactide, or mixtures thereof is more than 30 mol %. In another embodiment of the present invention, the overall conversion of lactic acid, lactide, or mixtures thereof is more than 40 mol %. In yet another embodiment of the present invention, the overall conversion of lactic acid, lactide, or mixtures thereof is more than 50 mol %. In even yet another embodiment of the present invention, the overall conversion of lactic acid, lactide, or mixtures thereof is more than 60 mol %. In one embodiment of the present invention, the overall conversion of lactic acid, lactide, or mixtures thereof is more than 80 mol %. In another embodiment of the present invention, the overall conversion of lactic acid, lactide, or mixtures thereof is more than 90 mol %.

When the conversion of the reactants in any step of the method of the present invention is low, recycling of the unreacted reactants may be implemented.

In one embodiment of the present invention, a method of making acrylic acid is provided. The method comprises the steps: (a) contacting a feed stream comprising lactic acid, lactide, or mixtures thereof with a first molten salt catalyst in a first reactor at a reaction temperature of about 120° C. and a reaction time of about 5 h to produce a first stream comprising 2-bromopropionic acid (2-BrPA) at a yield of about 60 mol % and with a selectivity of more than 95 mol %; (b) contacting said 2-BrPA with a second molten salt catalyst in a second reactor at a reaction temperature of about 160° C. and a second reaction time of about 20 h to produce a second stream comprising 3-bromopropionic acid (3-BrPA) at a yield of about 79 mol % and with a selectivity of about 89 mol %, and said acrylic acid at a yield of about 3 mol %; and (c) contacting said 3-BrPA with a trioctylamine (TOA) in a third reactor at a third reaction temperature of about 180° C. and a third reaction time of about 0.5 h to produce a third stream comprising said acrylic acid at a yield of about 90 mol % and with a selectivity of more than about 90 mol %; wherein said first molten salt catalyst comprises 3-methyl-1-(4-butane sulfonic acid) imidazolium bromide ([MIMBS]Br); wherein said [MIMBS]Br has a molar ratio to said lactic acid, lactide, or mixtures thereof of about 3:1; wherein said molten salt catalyst further comprises a 20 mmol HBr aqueous solution; wherein said second molten salt catalyst comprises tetrabutylphosphonium bromide ([PBu$_4$]Br); wherein said [PBu$_4$]Br and said 2-BrPA have a molar ratio of about 1:1; wherein said acrylic acid of said second stream is combined with said acrylic acid of said third stream into a production stream of said acrylic acid; and wherein said acrylic acid in said production stream has an overall acrylic acid yield of about 43 mol % and an overall acrylic acid selectivity of about 76 mol %.

In another embodiment of the present invention, a method of making acrylic acid is provided. The method comprises the steps: (a) contacting a feed stream comprising lactic acid, lactide, or mixtures thereof with a first molten salt catalyst in a first reactor at a reaction temperature of about 120° C. and a reaction time of about 5 h to produce a first stream comprising 2-bromopropionic acid (2-BrPA) at a yield of about 60 mol % and with a selectivity of more than 95 mol %; (b) contacting said 2-BrPA with a second molten salt catalyst in a second reactor at a reaction temperature of about 180° C. and a second reaction time of about 3 h to produce a second stream comprising 3-bromopropionic acid (3-BrPA) at a yield of about 52 mol % and with a selectivity of about 54 mol %, and said acrylic acid at a yield of about 45 mol %; and (c) contacting said 3-BrPA with a trioctylamine (TOA) in a third reactor at a third reaction temperature of about 180° C. and a third reaction time of about 0.5 h to produce a third stream comprising said acrylic acid at a yield of about 90 mol % and with a selectivity of more than about 90 mol %; wherein said first molten salt catalyst comprises 3-methyl-1-(4-butane sulfonic acid) imidazolium bromide ([MIMBS]Br); wherein said [MIMBS]Br has a molar ratio to said lactic acid, lactide, or mixtures thereof of about 3:1; wherein said molten salt catalyst further comprises a 20 mmol HBr aqueous solution; wherein said second molten salt catalyst comprises tetrabutylphosphonium bromide ([PBu$_4$]Br); wherein said [PBu$_4$]Br and said 2-BrPA have a molar ratio of about 9:1; wherein said acrylic acid of said second stream is combined with said acrylic acid of said third stream into a production stream of said acrylic acid; and wherein said acrylic acid in said production stream has an overall acrylic acid yield of about 55 mol % and an overall acrylic acid selectivity of about 83 mol %.

The feed stream can be introduced into the reactor with a simple tube or through atomization nozzles. Non-limiting examples of atomization nozzles comprise fan nozzles, pressure swirl atomizers, air blast atomizers, two-fluid atomizers, rotary atomizers, and supercritical carbon dioxide atomizers. In one embodiment of the present invention, the droplets of the feed stream are less than about 2 mm in diameter. In another embodiment of the present invention, the droplets of the feed stream are less than about 500 m in diameter. In yet another embodiment of the present invention, the droplets of the feed stream are less than about 200 m in diameter. In even yet another embodiment of the present invention, the droplets of the feed stream are less than about 100 m in diameter.

The product stream can be delivered out of the third reactor via a variety of methods. Non-limiting examples of methods of delivering the product stream out of the third reactor are evaporation, dilution, vacuum distillation, steam distillation, and gas stripping. Inert gases or carrier gases can be used in gas stripping. Non-limiting examples as strip gases are air, nitrogen, argon, carbon monoxide, carbon dioxide, and acetaldehyde. In one embodiment of the present invention, said contacting proceeds in the presence of a strip gas. In another embodiment of the present invention, said strip gas is selected from the group consisting of air, nitrogen, argon, carbon monoxide, and mixtures thereof.

The product stream produced from the third reactor is cooled to give a liquid acrylic acid stream as the product stream. The time required to cool the acrylic acid stream must be controlled to reduce acrylic acid polymerization. In one embodiment of the present invention, the residence time of the product stream in the cooling step is less than about 30 s. In another embodiment of the present invention, the residence time of the product stream in the cooling step is between about 0.1 s and about 60 s.

The product stream comprising acrylic acid, acrylic acid derivatives, or mixtures thereof produced according to the present invention can be purified using some or all of the processes of extraction, drying, distilling, cooling, partial melting, and decanting described in US20130274518A1 (incorporated herein by reference) to produce crude and glacial acrylic acid.

After purification, the crude and glacial acrylic acid can be polymerized to produce a superabsorbent polymer using processes that are similar to those described in US20130274697A1 (incorporated herein by reference).

IV Examples

The following Examples are provided to illustrate the invention, but are not intended to limit the scope thereof.

Comparative Examples 1 to 12 describe a one-step method of making acrylic acid using a molten salt catalyst comprising an ionic liquid (IL), containing a bromide anion (Br), and an acid, containing a bromine atom (Br), in the absence (Comparative Examples 1 and 2) or presence (Comparative Examples 3 to 12) of various phosphine oxides (PO).

Comparative Example 1—Acrylic Acid Synthesis from Lactide with [PBu$_4$]Br and 2-BrPA Molten Salt Catalyst, and Molar Ratio of Lactic Acid Equivalent (LAe) to [PBu$_4$]Br to 2-BrPA Equal to 10:10:1

17.31 g of solid tetrabutylphosphonium bromide ([PBu$_4$]Br; 50 mmol, 98%; Sigma-Aldrich Chemie GmbH, Taufkirchen, Germany; catalog #189138) and 3.6 g of solid lactide (25 mmol, L,L lactide, polymer grade, Corbion Purac Co., Lenexa, Kans.) were first mixed at room temperature and atmospheric conditions in a 100 mL three-necked glass reactor. 0.77 g of liquid 2-BrPA (5 mmol, 99%; Sigma-Aldrich Chemie GmbH, Taufkirchen, Germany; catalog # B78300) was then added to the reaction mixture, thus generating a molar ratio of lactic acid equivalent (LAe) to [PBu$_4$]Br to 2-BrPA equal to 10:10:1. The reaction mixture was then heated to a reaction temperature of 150° C. under continuous stirring with an overhead stirrer at a speed of 300 rpm. After the reaction mixture reached a constant temperature of 150° C., the system was batchwise refluxed and gaseous by-products were routed to the off-gas or collected in a hydrostatic column. After a reaction time of 48 h, the hot molten salt was analyzed via off-line $^1$H NMR (JEOL ECX 400 MHz). $^1$H qNMR analysis of the reaction mixture gave an acrylic acid yield (AAY) of about 47 mol %.

Comparative Example 2—Acrylic Acid Synthesis from Lactide with [PBu$_4$]Br and 2-BrPA Molten Salt Catalyst, and Molar Ratio of Lactic Acid Equivalent (LAe) to [PBu$_4$]Br to 2-BrPA Equal to 10:20:1

34.62 g of solid tetrabutylphosphonium bromide ([PBu$_4$]Br; 100 mmol, 98%; Sigma-Aldrich Chemie GmbH, Taufkirchen, Germany; catalog #189138) and 3.6 g of solid lactide (25 mmol, L,L lactide, polymer grade, Corbion Purac Co., Lenexa, Kans.) were first mixed at room temperature and atmospheric conditions in a 100 mL three-necked glass reactor. 0.77 g of liquid 2-BrPA (5 mmol, 99%; Sigma-Aldrich Chemie GmbH, Taufkirchen, Germany; catalog # B78300) was then added to the reaction mixture, thus generating a molar ratio of lactic acid equivalent (LAe) to [PBu$_4$]Br to 2-BrPA equal to 10:20:1. The reaction mixture was then heated to a reaction temperature of 150° C. under continuous stirring with an overhead stirrer at a speed of 300 rpm. After the reaction mixture reached a constant temperature of 150° C., the system was batchwise refluxed and gaseous by-products were routed to the off-gas or collected in a hydrostatic column. After a reaction time of 48 h, the hot molten salt was analyzed via off-line $^1$H NMR (JEOL ECX 400 MHz). $^1$H qNMR analysis of the reaction mixture gave an acrylic acid yield of about 52 mol % and an acrylic acid selectivity of about 72 mol %. When the reaction time was 8 h, the acrylic acid yield was about 22 mol % and the acrylic acid selectivity was about 65 mol %.

Tabulated results from Comparative Examples 1 and 2 can be seen in Table 1 below.

TABLE 1

| Example # | Molten Salt Catalyst - IL | Molten Salt Catalyst - Acid | Molar Ratio of IL to Acid, [—] | Reaction Time, [h] | Reaction Temperature, [° C.] | AAY, [mol %] |
|---|---|---|---|---|---|---|
| 1 | [PBu$_4$]Br | 2-BrPA | 10:1 | 48 | 150 | 47 |
| 2 | [PBu$_4$]Br | 2-BrPA | 20:1 | 48 | 150 | 52 |

Comparative Example 3—Acrylic Acid Synthesis from Lactide with [PBu$_4$]Br and 2-BrPA Molten Salt Catalyst, Molar Ratio of Lactic Acid Equivalent (LAe) to [PBu$_4$]Br to 2-BrPA Equal to 10:10:1, and in the Presence of TPPO 17.31 g of solid tetrabutylphosphonium bromide ([PBu$_4$]Br; 50 mmol, 98%; Sigma-Aldrich Chemie GmbH, Taufkirchen, Germany; catalog #189138) and 14.19 g of solid triphenylphosphine oxide (TPPO; 50 mmol, 98%; Sigma-Aldrich Chemie GmbH, Taufkirchen, Germany; catalog #172766) were first mixed at room temperature and atmospheric conditions in a 100 mL three-necked glass reactor. 3.6 g of solid lactide (25 mmol, L,L lactide, polymer grade, Corbion Purac Co., Lenexa, Kans.) and 0.77 g of liquid 2-BrPA (5 mmol, 99%; Sigma-Aldrich Chemie GmbH, Taufkirchen, Germany; catalog # B78300) were then added to the reaction mixture, thus generating a molar ratio of lactic acid equivalent (LAe) to [PBu$_4$]Br to 2-BrPA equal to 10:10:1. The reaction mixture was then heated to a reaction temperature of 150° C. under continuous stirring with an overhead stirrer at a speed of 300 rpm. After the reaction mixture reached a constant reaction temperature of 150° C., the system was batchwise refluxed and gaseous by-products were routed to the off-gas or collected in a hydrostatic column. After a reaction time of 192 h, the hot molten salt was analyzed via off-line $^1$H NMR (JEOL ECX 400 MHz). $^1$H qNMR analysis of the reaction mixture gave an acrylic acid yield of about 45 mol %.

Comparative Example 4—Acrylic Acid Synthesis from Lactide with [PBu$_4$]Br and 2-BrPA Molten Salt Catalyst, Molar Ratio of Lactic Acid Equivalent (LAe) to [PBu$_4$]Br to 2-BrPA Equal to 10:10:1, and in the Presence of TBPO 17.31 g of solid tetrabutylphosphonium bromide ([PBu$_4$]Br; 50 mmol, 98%; Sigma-Aldrich Chemie GmbH, Taufkirchen, Germany; catalog #189138) and 11.49 g of solid tributylphosphine oxide (TBPO; 50 mmol, 95%; Sigma-Aldrich Chemie GmbH, Taufkirchen, Germany; catalog #172766) were first mixed at room temperature and atmospheric conditions in a 100 mL three-necked glass reactor. 3.6 g of solid lactide (25 mmol, L,L lactide, polymer grade, Corbion Purac Co., Lenexa, Kans.) and 0.77 g of liquid 2-BrPA (5 mmol, 99%; Sigma-Aldrich Chemie GmbH, Taufkirchen, Germany; catalog # B78300) were then added to the reaction mixture, thus generating a molar ratio of lactic acid equivalent (LAe) to [PBu$_4$]Br to 2-BrPA equal to 10:10:1. The reaction mixture was then heated to a reaction temperature of 150° C. under continuous stirring with an overhead stirrer at a speed of 300 rpm. After the reaction mixture reached a constant temperature of 150° C., the system was batchwise refluxed and gaseous by-products were routed to the off-gas or collected in a hydrostatic column. After a reaction time of 144 h, the hot molten salt was analyzed via off-line $^1$H NMR (JEOL ECX 400 MHz). $^1$H qNMR analysis of the reaction mixture gave an acrylic acid yield of about 52 mol %.

Comparative Example 5—Acrylic Acid Synthesis from Lactide with [PBu$_4$]Br and 2-BrPA Molten Salt Catalyst, Molar Ratio of Lactic Acid Equivalent (LAe) to [PBu$_4$]Br to 2-BrPA Equal to 10:10:1, in the Presence of TOPO, at 140° C., and in 192 h Reaction Time 17.31 g of solid tetrabutylphosphonium bromide ([PBu$_4$]Br; 50 mmol, 98%; Sigma-Aldrich Chemie GmbH, Taufkirchen, Germany; catalog #189138) and 19.53 g of solid trioctylphosphine oxide (TOPO; 50 mmol, 99%; Sigma-Aldrich Chemie GmbH, Taufkirchen, Germany; catalog #172766) were first mixed at room temperature and atmospheric conditions in a 100 mL three-necked glass reactor. 3.6 g of solid lactide (25 mmol, L,L lactide, polymer grade, Corbion Purac Co., Lenexa, Kans.) and 0.77 g of liquid 2-BrPA (5 mmol, 99%; Sigma-Aldrich Chemie GmbH, Taufkirchen, Germany; catalog # B78300) were then added to the reaction mixture, thus generating a molar ratio of lactic acid equivalent (LAe) to [PBu$_4$]Br to 2-BrPA equal to 10:10:1. The reaction mixture was then heated to a reaction temperature of 140° C. under continuous stirring with an overhead stirrer at a speed of 300 rpm. After the reaction mixture reached a constant temperature of 140° C., the system was batchwise refluxed and gaseous by-products were routed to the off-gas or collected in a hydrostatic column. After a reaction time of 192 h, the hot molten salt was analyzed via off-line $^1$H NMR (JEOL ECX 400 MHz). $^1$H qNMR analysis of the reaction mixture gave an acrylic acid yield of about 33 mol %.

Comparative Example 6—Acrylic Acid Synthesis from Lactide with [PBu$_4$]Br and 2-BrPA Molten Salt Catalyst, Molar Ratio of Lactic Acid Equivalent (LAe) to [PBu$_4$]Br to 2-BrPA Equal to 10:10:1, in the Presence of TOPO, at 150° C., and in 192 h Reaction Time 17.31 g of solid tetrabutylphosphonium bromide ([PBu$_4$]Br; 50 mmol, 98%; Sigma-Aldrich Chemie GmbH, Taufkirchen, Germany; catalog #189138) and 19.53 g of solid trioctylphosphine oxide (TOPO; 50 mmol, 99%; Sigma-Aldrich Chemie GmbH, Taufkirchen, Germany; catalog #172766) were first mixed at room temperature and atmospheric conditions in a 100 mL three-necked glass reactor. 3.6 g of solid lactide (25 mmol, L,L lactide, polymer grade, Corbion Purac Co., Lenexa, Kans.) and 0.77 g of liquid 2-BrPA (5 mmol, 99%; Sigma-Aldrich Chemie GmbH, Taufkirchen, Germany; catalog # B78300) were then added to the reaction mixture, thus generating a molar ratio of lactic acid equivalent (LAe) to [PBu$_4$]Br to 2-BrPA equal to 10:10:1. The reaction mixture was then heated to a reaction temperature of 150° C. under continuous stirring with an overhead stirrer at a speed of 300 rpm. After the reaction mixture reached a constant temperature of 150° C., the system was batchwise refluxed and gaseous by-products were routed to the off-gas or collected in a hydrostatic column. After a reaction time of 192 h, the hot molten salt was analyzed via off-line $^1$H NMR (JEOL ECX 400 MHz). $^1$H qNMR analysis of the reaction mixture gave an acrylic acid yield of about 45 mol %.

Comparative Example 7—Acrylic Acid Synthesis from Lactide with [PBu$_4$]Br and 2-BrPA Molten Salt Catalyst, Molar Ratio of Lactic Acid Equivalent (LAe) to [PBu$_4$]Br to 2-BrPA Equal to 10:10:1, in the Presence of TOPO, at 160° C., and in 72 h Reaction Time 17.31 g of solid tetrabutylphosphonium bromide ([PBu$_4$]Br; 50 mmol, 98%; Sigma-Aldrich Chemie GmbH, Taufkirchen, Germany; catalog #189138) and 19.53 g of solid trioctylphosphine oxide (TOPO; 50 mmol, 99%; Sigma-Aldrich Chemie GmbH, Taufkirchen, Germany; catalog #172766) were first mixed at room temperature and atmospheric conditions in a 100 mL three-necked glass reactor. 3.6 g of solid lactide (25 mmol, L,L lactide, polymer grade, Corbion Purac Co., Lenexa, Kans.) and 0.77 g of liquid 2-BrPA (5 mmol, 99%; Sigma-Aldrich Chemie GmbH, Taufkirchen, Germany; catalog # B78300) were then added to the reaction mixture, thus generating a molar ratio of lactic acid equivalent (LAe) to [PBu$_4$]Br to 2-BrPA equal to 10:10:1. The reaction mixture was heated to a reaction temperature of 160° C. under continuous stirring with an overhead stirrer at a speed of 300 rpm. After the reaction mixture reached a constant temperature of 160° C., the system was batchwise refluxed and gaseous by-products were routed to the off-gas or collected in a hydrostatic column. After a reaction time of 72 h, the hot molten salt was analyzed via off-line $^1$H NMR (JEOL ECX 400 MHz). $^1$H qNMR analysis of the reaction mixture gave an acrylic acid yield of about 50 mol %.

Comparative Example 8—Acrylic Acid Synthesis from Lactide with [PBu$_4$]Br and 2-BrPA Molten Salt Catalyst, Molar Ratio of Lactic Acid Equivalent (LAe) to [PBu$_4$]Br to 2-BrPA Equal to 20:10:1, in the Presence of TOPO, at 150° C., and in 24 h Reaction Time 17.31 g of solid tetrabutylphosphonium bromide ([PBu$_4$]Br; 50 mmol, 98%; Sigma-Aldrich Chemie GmbH, Taufkirchen, Germany; catalog #189138) and 19.53 g of solid trioctylphosphine oxide (TOPO; 50 mmol, 99%; Sigma-Aldrich Chemie GmbH, Taufkirchen, Germany; catalog #172766) were first mixed at room temperature and atmospheric conditions in a 100 mL three-necked glass reactor. 7.2 g of solid lactide (50 mmol, L,L lactide, polymer grade, Corbion Purac Co., Lenexa, Kans.) and 0.77 g of liquid 2-BrPA (5 mmol, 99%; Sigma-Aldrich Chemie GmbH, Taufkirchen, Germany; catalog # B78300) were then added to the reaction mixture, thus generating a molar ratio of lactic acid equivalent (LAe) to [PBu$_4$]Br to 2-BrPA equal to 20:10:1. The reaction mixture was heated to a reaction temperature of 150° C. under continuous stirring with an overhead stirrer at a speed of 300 rpm. After the reaction mixture reached a constant temperature of 150° C., the system was batchwise refluxed and gaseous by-products were routed to the off-gas or collected in a hydrostatic column. After a reaction time of 24 h, the hot molten salt was analyzed via off-line $^1$H NMR (JEOL ECX 400 MHz). $^1$H qNMR analysis of the reaction mixture gave an acrylic acid yield of about 12 mol %.

Comparative Example 9—Acrylic Acid Synthesis from Lactide with [PBu$_4$]Br and 2-BrPA Molten Salt Catalyst, Molar Ratio of Lactic Acid Equivalent (LAe) to [PBu$_4$]Br to 2-BrPA Equal to 10:10:1, in the Presence of TOPO, at 150° C., and in 24 h Reaction Time 17.31 g of solid tetrabutylphosphonium bromide ([PBu$_4$]Br; 50 mmol, 98%; Sigma-Aldrich Chemie GmbH, Taufkirchen, Germany; catalog #189138) and 19.53 g of solid trioctylphosphine oxide (TOPO; 50 mmol, 99%; Sigma-Aldrich Chemie GmbH, Taufkirchen, Germany; catalog #172766) were first mixed at room temperature and atmospheric conditions in a 100 mL three-necked glass reactor. 3.6 g of solid lactide (25 mmol, L,L lactide, polymer grade, Corbion Purac Co., Lenexa, Kans.) and 0.77 g of liquid 2-BrPA (5 mmol, 99%; Sigma-Aldrich Chemie GmbH, Taufkirchen, Germany; catalog # B78300) were then added to the reaction mixture, thus generating a molar ratio of lactic acid equivalent (LAe) to [PBu$_4$]Br to 2-BrPA equal to 10:10:1. The reaction mixture was heated to a reaction temperature of 150° C. under continuous stirring with an overhead stirrer at a speed of 300 rpm. After the reaction mixture reached a constant temperature of 150° C., the system was batchwise refluxed and gaseous by-products were routed to the off-gas or collected in a hydrostatic column. After a reaction time of 24 h, the hot molten salt was analyzed via off-line $^1$H NMR (JEOL ECX 400 MHz). $^1$H qNMR analysis of the reaction mixture gave an acrylic acid yield of about 21 mol %.

Comparative Example 10—Acrylic Acid Synthesis from Lactide with [PBu$_4$]Br and 2-BrPA Molten Salt Catalyst, Molar Ratio of Lactic Acid Equivalent (LAe) to [PBu$_4$]Br to 2-BrPA Equal to 5:10:1, in the Presence of TOPO, at 150° C., and in 24 h Reaction Time 17.31 g of solid tetrabutylphosphonium bromide ([PBu$_4$]Br; 50 mmol, 98%; Sigma-Aldrich Chemie GmbH, Taufkirchen, Germany; catalog #189138) and 19.53 g of solid trioctylphosphine oxide (TOPO; 50 mmol, 99%; Sigma-Aldrich Chemie GmbH, Taufkirchen, Germany; catalog #172766) were first mixed at room temperature and atmospheric conditions in a 100 mL three-necked glass reactor. 1.8 g of solid lactide (12.5 mmol, L,L lactide, polymer grade, Corbion Purac Co., Lenexa, Kans.) and 0.77 g of liquid 2-BrPA (5 mmol, 99%; Sigma-Aldrich Chemie GmbH, Taufkirchen, Germany; catalog # B78300) were then added to the reaction mixture, thus generating a molar ratio of lactic acid equivalent (LAe) to [PBu$_4$]Br to 2-BrPA equal to 5:10:1. The reaction mixture was heated to a reaction temperature of 150° C. under continuous stirring with an overhead stirrer at a speed of 300 rpm. After the reaction mixture reached a constant temperature of 150° C., the system was batchwise refluxed and gaseous by-products were routed to the off-gas or collected in a hydrostatic column. After a reaction time of 24 h, the hot molten salt was analyzed via off-line $^1$H NMR (JEOL ECX 400 MHz). $^1$H qNMR analysis of the reaction mixture gave an acrylic acid yield of about 27 mol %.

Comparative Example 11—Acrylic Acid Synthesis from Lactide with [PBu4]Br and 2-BrPA Molten Salt Catalyst, Molar Ratio of Lactic Acid Equivalent (LAe) to [PBu4]Br to 2-BrPA Equal to 20:40:1, in the Presence of TOPO, at 150° C., and in 24 h Reaction Time 17.31 g of solid tetrabutylphosphonium bromide ([PBu4]Br; 50 mmol, 98%; Sigma-Aldrich Chemie GmbH, Taufkirchen, Germany; catalog #189138) and 19.53 g of solid trioctylphosphine oxide (TOPO; 50 mmol, 99%; Sigma-Aldrich Chemie GmbH, Taufkirchen, Germany; catalog #172766) were first mixed at room temperature and atmospheric conditions in a 100 mL three-necked glass reactor. 1.8 g of solid lactide (12.5 mmol, L,L lactide, polymer grade, Corbion Purac Co., Lenexa, Kans.) and 0.1925 g of liquid 2-BrPA (1.25 mmol, 99%; Sigma-Aldrich Chemie GmbH, Taufkirchen, Germany; catalog # B78300) were then added to the reaction mixture, thus generating a molar ratio of lactic acid equivalent (LAe) to [PBu4]Br to 2-BrPA equal to 20:40:1. The reaction mixture was heated to a reaction temperature of 150° C. under continuous stirring with an overhead stirrer at a speed of 300 rpm. After the reaction mixture reached a constant temperature of 150° C., the system was batchwise refluxed and gaseous by-products were routed to the off-gas or collected in a hydrostatic column. After a reaction time of 24 h, the hot molten salt was analyzed via off-line $^1$H NMR (JEOL ECX 400 MHz). $^1$H qNMR analysis of the reaction mixture gave an acrylic acid yield of about 16 mol %.

Comparative Example 12—Acrylic Acid Synthesis from Lactide with [PBu4]Br and 2-BrPA Molten Salt Catalyst, Molar Ratio of Lactic Acid Equivalent (LAe) to [PBu4]Br to 2-BrPA Equal to 10:20:1, in the Presence of TOPO, at 150° C., and in 24 h Reaction Time 17.31 g of solid tetrabutylphosphonium bromide ([PBu4]Br; 50 mmol, 98%; Sigma-Aldrich Chemie GmbH, Taufkirchen, Germany; catalog #189138) and 19.53 g of solid trioctylphosphine oxide (TOPO; 50 mmol, 99%; Sigma-Aldrich Chemie GmbH, Taufkirchen, Germany; catalog #172766) were first mixed at room temperature and atmospheric conditions in a 100 mL three-necked glass reactor. 1.8 g of solid lactide (12.5 mmol, L,L lactide, polymer grade, Corbion Purac Co., Lenexa, Kans.) and 0.385 g of liquid 2-BrPA (2.5 mmol, 99%; Sigma-Aldrich Chemie GmbH, Taufkirchen, Germany; catalog # B78300) were then added to the reaction mixture, thus generating a molar ratio of lactic acid equivalent (LAe) to [PBu4]Br to 2-BrPA equal to 10:20:1. The reaction mixture was heated to a reaction temperature of 150° C. under continuous stirring with an overhead stirrer at a speed of 300 rpm. After the reaction mixture reached a constant temperature of 150° C., the system was batchwise refluxed and gaseous by-products were routed to the off-gas or collected in a hydrostatic column. After a reaction time of 24 h, the hot molten salt was analyzed via off-line $^1$H NMR (JEOL ECX 400 MHz). $^1$H qNMR analysis of the reaction mixture gave an acrylic acid yield of about 18 mol %.

Tabulated results from Comparative Examples 3 to 12 can be seen in Table 2 below.

TABLE 2

| Example # | Molten Salt Catalyst - IL + Acid | Molar Ratio of LAe:IL:Acid | PO; Molar Ratio of PO:IL | Reaction Time, [h] | Reaction Temperature, [° C.] | AAY, [mol %] |
|---|---|---|---|---|---|---|
| 3 | [PBu4]Br + 2-BrPA | 10:10:1 | TPPO; 1:1 | 192 | 150 | 45 |
| 4 | [PBu4]Br + 2-BrPA | 10:10:1 | TBPO; 1:1 | 144 | 150 | 52 |
| 5 | [PBu4]Br + 2-BrPA | 10:10:1 | TOPO; 1:1 | 192 | 140 | 33 |
| 6 | [PBu4]Br + 2-BrPA | 10:10:1 | TOPO; 1:1 | 192 | 150 | 45 |
| 7 | [PBu4]Br + 2-BrPA | 10:10:1 | TOPO; 1:1 | 72 | 160 | 50 |
| 8 | [PBu4]Br + 2-BrPA | 20:10:1 | TOPO; 1:1 | 24 | 150 | 12 |
| 9 | [PBu4]Br + 2-BrPA | 10:10:1 | TOPO; 1:1 | 24 | 150 | 21 |
| 10 | [PBu4]Br + 2-BrPA | 5:10:1 | TOPO; 1:1 | 24 | 150 | 27 |
| 11 | [PBu4]Br + 2-BrPA | 20:40:1 | TOPO; 1:1 | 24 | 150 | 16 |
| 12 | [PBu4]Br + 2-BrPA | 10:20:1 | TOPO; 1:1 | 24 | 150 | 18 |

Examples 13 to 22 describe step 1 of the inventive method that produces 2-BrPA (see also FIG. 1). Comparative Examples 23 to 28 describe the production of 2-BrPA not according to this invention. Examples 29 to 54 describe step 2 of the inventive method that converts 2-BrPA to 3-BrPA and acrylic acid (see also FIG. 1). Finally, Examples 55 and 56 describe step 3 of the inventive method that converts 3-BrPA to acrylic acid (see also FIG. 1).

Example 13—2-BrPA Synthesis from Lactide with [MIMBS]Br Molten Salt Catalyst and Readjustment of the HBr Amount 16.370 g of solid MIMBS (75 mmol, J. Mater. Chem., 2001, 11, 1057-1062), 12.642 g of 48 wt % hydrobromic acid (HBr; 75 mmol, 48%; Sigma-Aldrich Chemie GmbH, Taufkirchen, Germany; catalog #244260), and 64 g of cyclohexane ($C_6H_{12}$, 0.76 mol, >99.5%, Sigma-Aldrich Chemie GmbH, Taufkirchen, Germany; catalog #33117) were mixed at room temperature and atmospheric conditions in a 100 mL three-necked glass reactor to produce a biphasic reaction mixture, which was then heated to a temperature of 69.8° C. under continuous stirring with a magnetic stirring bar at a speed of 600 rpm. The protic and HBr-loaded ionic liquid [MIMBS]Br was isolated by removing the water using a Dean-Stark-apparatus with external heating to 90° C. and finally decanting the cyclohexane phase after the glass reactor was cooled down to room temperature. After reaction, the desired acid amount (75 mmol) was readjusted by adding 3.4 g of 48% hydrobromic acid (HBr; 20 mmol, 48%; Sigma-Aldrich Chemie GmbH, Taufkirchen, Germany; catalog #244260). 1.8 g of solid lactide (12.5 mmol, L,L lactide, polymer grade, Corbion Purac Co., Lenexa, Kans.) were added to the reactor and the activated reaction mixture was heated to 120° C. under continuous stirring with an overhead stirrer at a speed of 600 rpm. The reaction mixture was batchwise refluxed and gaseous by-products were routed to the off-gas or collected in a hydrostatic column. After a reaction time of 5 h, the reaction mixture was quenched with 7.92 g of methanol (CH$_3$OH, 0.25 mol, 99.8%, anhydrous, Sigma-Aldrich Chemie GmbH, Taufkirchen, Germany; catalog #322415) and was analyzed via off-line $^1$H NMR (JEOL ECX 400 MHz). $^1$H qNMR analysis of the reaction mixture gave a 2-BrPA yield of about 60 mol % and selectivity of more than about 95 mol %.

Example 14—2-BrPA Synthesis from Lactide with [MIMBS]Br Molten Salt Catalyst, No Water Added, and No Readjustment of the HBr Amount 16.370 g of solid MIMBS (75 mmol, *J. Mater. Chem.*, 2001, 11, 1057-1062), 12.642 g of 48 wt % hydrobromic acid (HBr; 75 mmol, 48%; Sigma-Aldrich Chemie GmbH, Taufkirchen, Germany; catalog #244260), and 64 g of cyclohexane (C$_6$H$_{12}$, 0.76 mol, >99.5%, Sigma-Aldrich Chemie GmbH, Taufkirchen, Germany; catalog #33117) were mixed at room temperature and atmospheric conditions in a 100 mL three-necked glass reactor to produce a biphasic reaction mixture, which was then heated to a temperature of 69.8° C. under continuous stirring with a magnetic stirring bar at a speed of 600 rpm. The protic and HBr-loaded ionic liquid [MIMBS]Br was isolated by removing the water using a Dean-Stark-apparatus with external heating to 90° C. and finally decanting the cyclohexane phase after the glass reactor was cooled down to room temperature. 1.8 g of solid lactide (12.5 mmol, L,L lactide, polymer grade, Corbion Purac Co., Lenexa, Kans.) were added to the reactor and the activated reaction mixture was heated to 120° C. under continuous stirring with an overhead stirrer at a speed of 600 rpm. The reaction mixture was batchwise refluxed and gaseous by-products were routed to the off-gas or collected in a hydrostatic column. After a reaction time of 5 h, the reaction mixture was quenched with 7.92 g of methanol (CH$_3$OH, 0.25 mol, 99.8%, anhydrous, Sigma-Aldrich Chemie GmbH, Taufkirchen, Germany; catalog #322415) and was analyzed via off-line $^1$H NMR (JEOL ECX 400 MHz). $^1$H qNMR analysis of the reaction mixture gave a 2-BrPA yield of about 48 mol % and selectivity of more than about 95 mol %.

Example 15—2-BrPA Synthesis from Lactide with [MIMBS]Br Molten Salt Catalyst, 1 g of Water Added, and No Readjustment of the HBr Amount 16.370 g of solid MIMBS (75 mmol, *J. Mater. Chem.*, 2001, 11, 1057-1062), 12.642 g of 48 wt % hydrobromic acid (HBr; 75 mmol, 48%; Sigma-Aldrich Chemie GmbH, Taufkirchen, Germany; catalog #244260), and 64 g of cyclohexane (C$_6$H$_{12}$, 0.76 mol, >99.5%, Sigma-Aldrich Chemie GmbH, Taufkirchen, Germany; catalog #33117) were mixed at room temperature and atmospheric conditions in a 100 mL three-necked glass reactor to produce a biphasic reaction mixture, which was then heated to a temperature of 69.8° C. under continuous stirring with a magnetic stirring bar at a speed of 600 rpm. The protic and HBr-loaded ionic liquid [MIMBS]Br was isolated by removing the water using a Dean-Stark-apparatus with external heating to 90° C. and finally decanting the cyclohexane phase after the glass reactor was cooled down to room temperature. After reaction, 1 g of water was added. 1.8 g of solid lactide (12.5 mmol, L,L lactide, polymer grade, Corbion Purac Co., Lenexa, Kans.) were added to the reactor and the activated reaction mixture was heated to 120° C. under continuous stirring with an overhead stirrer at a speed of 600 rpm. The reaction mixture was batchwise refluxed and gaseous by-products were routed to the off-gas or collected in a hydrostatic column. After a reaction time of 5 h, the reaction mixture was quenched with 7.92 g of methanol (CH$_3$OH, 0.25 mol, 99.8%, anhydrous, Sigma-Aldrich Chemie GmbH, Taufkirchen, Germany; catalog #322415) and was analyzed via off-line $^1$H NMR (JEOL ECX 400 MHz). $^1$H qNMR analysis of the reaction mixture gave a 2-BrPA yield of about 29 mol % and selectivity of more than about 95 mol %.

Example 16—2-BrPA Synthesis from Lactide with [MIMBS]Br Molten Salt Catalyst, 4 g of Water Added, and No Readjustment of the HBr Amount 16.370 g of solid MIMBS (75 mmol, *J. Mater. Chem.*, 2001, 11, 1057-1062), 12.642 g of 48 wt % hydrobromic acid (HBr; 75 mmol, 48%; Sigma-Aldrich Chemie GmbH, Taufkirchen, Germany; catalog #244260), and 64 g of cyclohexane (C$_6$H$_{12}$, 0.76 mol, >99.5%, Sigma-Aldrich Chemie GmbH, Taufkirchen, Germany; catalog #33117) were mixed at room temperature and atmospheric conditions in a 100 mL three-necked glass reactor to produce a biphasic reaction mixture, which was then heated to a temperature of 69.8° C. under continuous stirring with a magnetic stirring bar at a speed of 600 rpm. The protic and HBr-loaded ionic liquid [MIMBS]Br was isolated by removing the water using a Dean-Stark-apparatus with external heating to 90° C. and finally decanting the cyclohexane phase after the glass reactor was cooled down to room temperature. After reaction, 4 g of water were added. 1.8 g of solid lactide (12.5 mmol, L,L lactide, polymer grade, Corbion Purac Co., Lenexa, Kans.) were added to the reactor and the activated reaction mixture was heated to 120° C. under continuous stirring with an overhead stirrer at a speed of 600 rpm. The reaction mixture was batchwise refluxed and gaseous by-products were routed to the off-gas or collected in a hydrostatic column. After a reaction time of 5 h, the reaction mixture was quenched with 7.92 g of methanol (CH$_3$OH, 0.25 mol, 99.8%, anhydrous, Sigma-Aldrich Chemie GmbH, Taufkirchen, Germany; catalog #322415) and was analyzed via off-line $^1$H NMR (JEOL ECX 400 MHz). $^1$H qNMR analysis of the reaction mixture gave a 2-BrPA yield of about 14 mol % and selectivity of more than about 95 mol %.

Tabulated results from Examples 13 to 16 can be seen in Table 3 below (2-BrPAY is 2-BrPA Yield, and 2-BrPAS is 2-BrPA Selectivity), where lactide was the feed material.

TABLE 3

| Example # | IL | Additional Water or HBr? | Reaction Time, [h] | Reaction Temp., [° C.] | 2-BrPAY, [mol %] | 2-BrPAS, [mol %] |
|---|---|---|---|---|---|---|
| 13 | [MIMBS]Br | 20 mmol HBr solution | 5 | 120 | 60 | >95 |
| 14 | [MIMBS]Br | no water; no HBr | 5 | 120 | 48 | >95 |
| 15 | [MIMBS]Br | 1 g water; no HBr | 5 | 120 | 29 | >95 |
| 16 | [MIMBS]Br | 4 g water; no HBr | 5 | 120 | 14 | >95 |

Example 17—2-BrPA Synthesis at 140° C. from Lactide with [MIMBS]Br Molten Salt Catalyst, No Water Added, and No Readjustment of the HBr Amount 16.370 g of solid MIMBS (75 mmol, *J. Mater. Chem.*, 2001, 11, 1057-1062), 12.642 g of 48 wt % hydrobromic acid (HBr; 75 mmol, 48%; Sigma-Aldrich Chemie GmbH, Taufkirchen, Germany; catalog #244260), and 64 g of cyclohexane ($C_6H_{12}$, 0.76 mol, >99.5%, Sigma-Aldrich Chemie GmbH, Taufkirchen, Germany; catalog #33117) were mixed at room temperature and atmospheric conditions in a 100 mL three-necked glass reactor to produce a biphasic reaction mixture, which was then heated to a temperature of 69.8° C. under continuous stirring with a magnetic stirring bar at a speed of 600 rpm. The protic and HBr loaded ionic liquid [MIMBS]Br was isolated by removing the water using a Dean-Stark-apparatus with external heating to 100° C. and finally decanting the cyclohexane phase after the glass reactor was cooled down to room temperature. 1.8 g of solid lactide (12.5 mmol; L,L lactide, polymer grade; Corbion Purac Co., Lenexa, Kans.) were added to the reactor and the activated reaction mixture was heated to 140° C. under continuous stirring with an overhead stirrer at a speed of 600 rpm. The reaction mixture was batchwise refluxed and gaseous by-products were routed to the off-gas or collected in a hydrostatic column. After a reaction time of 5 h, the reaction mixture was quenched with 7.92 g of methanol ($CH_3OH$, 0.25 mol, 99.8%, anhydrous, Sigma-Aldrich Chemie GmbH, Taufkirchen, Germany; catalog #322415) and was analyzed via off-line $^1H$ NMR (JEOL ECX 400 MHz). $^1H$ qNMR analysis of the reaction mixture gave a 2-BrPA yield of about 25 mol % and selectivity of about 77 mol %.

Example 18—2-BrPA Synthesis at 120° C. from Lactide with [MIMBS]Br Molten Salt Catalyst, No Water Added, and No Readjustment of the HBr Amount 16.370 g of solid MIMBS (75 mmol, *J. Mater. Chem.*, 2001, 11, 1057-1062), 12.642 g of 48 wt % hydrobromic acid (HBr; 75 mmol, 48%; Sigma-Aldrich Chemie GmbH, Taufkirchen, Germany; catalog #244260), and 64 g of cyclohexane ($C_6H_{12}$, 0.76 mol, >99.5%, Sigma-Aldrich Chemie GmbH, Taufkirchen, Germany; catalog #33117) were mixed at room temperature and atmospheric conditions in a 100 mL three-necked glass reactor to produce a biphasic reaction mixture, which was then heated to a temperature of 69.8° C. under continuous stirring with a magnetic stirring bar at a speed of 600 rpm. The protic and HBr loaded ionic liquid [MIMBS]Br was isolated by removing the water using a Dean-Stark-apparatus with external heating to 100° C. and finally decanting the cyclohexane phase after the glass reactor was cooled down to room temperature. 1.8 g of solid lactide (12.5 mmol; L,L lactide, polymer grade; Corbion Purac Co., Lenexa, Kans.) were added to the reactor and the activated reaction mixture was heated to 120° C. under continuous stirring with an overhead stirrer at a speed of 600 rpm. The reaction mixture was batchwise refluxed and gaseous by-products were routed to the off-gas or collected in a hydrostatic column. After a reaction time of 5 h, the reaction mixture was quenched with 7.92 g of methanol ($CH_3OH$, 0.25 mol, 99.8%, anhydrous, Sigma-Aldrich Chemie GmbH, Taufkirchen, Germany; catalog #322415) and was analyzed via off-line $^1H$ NMR (JEOL ECX 400 MHz). $^1H$ qNMR analysis of the reaction mixture gave a 2-BrPA yield of about 32 mol % and selectivity of more than about 90 mol %.

Example 19—2-BrPA Synthesis at 100° C. from Lactide with [MIMBS]Br Molten Salt Catalyst, No Water Added, and No Readjustment of the HBr Amount 16.370 g of solid MIMBS (75 mmol, *J. Mater. Chem.*, 2001, 11, 1057-1062), 12.642 g of 48 wt % hydrobromic acid (HBr; 75 mmol, 48%; Sigma-Aldrich Chemie GmbH, Taufkirchen, Germany; catalog #244260), and 64 g of cyclohexane ($C_6H_{12}$, 0.76 mol, >99.5%, Sigma-Aldrich Chemie GmbH, Taufkirchen, Germany; catalog #33117) were mixed at room temperature and atmospheric conditions in a 100 mL three-necked glass reactor to produce a biphasic reaction mixture, which was then heated to a temperature of 69.8° C. under continuous stirring with a magnetic stirring bar at a speed of 600 rpm. The protic and HBr loaded ionic liquid [MIMBS]Br was isolated by removing the water using a Dean-Stark-apparatus with external heating to 100° C. and finally decanting the cyclohexane phase after the glass reactor was cooled down to room temperature. 1.8 g of solid lactide (12.5 mmol; L,L lactide, polymer grade; Corbion Purac Co., Lenexa, Kans.) were added to the reactor and the activated reaction mixture was heated to 100° C. under continuous stirring with an overhead stirrer at a speed of 600 rpm. The reaction mixture was batchwise refluxed and gaseous by-products were routed to the off-gas or collected in a hydrostatic column. After a reaction time of 5 h, the reaction mixture was quenched with 7.92 g of methanol ($CH_3OH$, 0.25 mol, 99.8%, anhydrous, Sigma-Aldrich Chemie GmbH, Taufkirchen, Germany; catalog #322415) and was analyzed via off-line $^1H$ NMR (JEOL ECX 400 MHz). $^1H$ qNMR analysis of the reaction mixture gave a 2-BrPA yield of about 16 mol % and selectivity of more than about 90 mol %.

Example 20—2-BrPA Synthesis at 140° C. from Lactic Acid with [MIMBS]Br Molten Salt Catalyst, No Water Added, and No Readjustment of the HBr Amount 16.370 g of solid MIMBS (75 mmol, *J. Mater. Chem.*, 2001, 11, 1057-1062), 12.642 g of 48 wt % hydrobromic acid (HBr; 75 mmol, 48%; Sigma-Aldrich Chemie GmbH, Taufkirchen, Germany; catalog #244260), and 64 g of cyclohexane ($C_6H_{12}$, 0.76 mol, >99.5%, Sigma-Aldrich Chemie GmbH, Taufkirchen, Germany; catalog #33117) were mixed at room temperature and atmospheric conditions in a 100 mL three-necked glass reactor to produce a biphasic reaction mixture, which was then heated to a temperature of 69.8° C. under continuous stirring with a magnetic stirring bar at a speed of 600 rpm. The protic and HBr loaded ionic liquid [MIMBS]Br was isolated by removing the water using a Dean-Stark-apparatus with external heating to 100° C. and finally decanting the cyclohexane phase after the glass reactor was cooled down to room temperature. 2.559 g of an 88 wt % L-lactic acid solution (25 mmol; Corbion Purac Co., Lenexa, Kans.) were added to the reactor and the activated reaction mixture was heated to 140° C. under continuous stirring with an overhead stirrer at a speed of 600 rpm. The reaction mixture was batchwise refluxed and gaseous by-products were routed to the off-gas or collected in a hydrostatic column. After a reaction time of 5 h, the reaction mixture was quenched with 7.92 g of methanol (CH$_3$OH, 0.25 mol, 99.8%, anhydrous, Sigma-Aldrich Chemie GmbH, Taufkirchen, Germany; catalog #322415) and was analyzed via off-line $^1$H NMR (JEOL ECX 400 MHz). $^1$H qNMR analysis of the reaction mixture gave a 2-BrPA yield of about 32 mol % and selectivity of about 74 mol %.

Example 21—2-BrPA Synthesis at 120° C. from Lactic Acid with [MIMBS]Br Molten Salt Catalyst, No Water Added, and No Readjustment of the HBr Amount 16.370 g of solid MIMBS (75 mmol, *J. Mater. Chem.*, 2001, 11, 1057-1062), 12.642 g of 48 wt % hydrobromic acid (HBr; 75 mmol, 48%; Sigma-Aldrich Chemie GmbH, Taufkirchen, Germany; catalog #244260), and 64 g of cyclohexane (C$_6$H$_{12}$, 0.76 mol, >99.5%, Sigma-Aldrich Chemie GmbH, Taufkirchen, Germany; catalog #33117) were mixed at room temperature and atmospheric conditions in a 100 mL three-necked glass reactor to produce a biphasic reaction mixture, which was then heated to a temperature of 69.8° C. under continuous stirring with a magnetic stirring bar at a speed of 600 rpm. The protic and HBr loaded ionic liquid [MIMBS]Br was isolated by removing the water using a Dean-Stark-apparatus with external heating to 100° C. and finally decanting the cyclohexane phase after the glass reactor was cooled down to room temperature. 2.559 g of an 88 wt % L-lactic acid solution (25 mmol; Corbion Purac Co., Lenexa, Kans.) were added to the reactor and the activated reaction mixture was heated to 120° C. under continuous stirring with an overhead stirrer at a speed of 600 rpm. The reaction mixture was batchwise refluxed and gaseous by-products were routed to the off-gas or collected in a hydrostatic column. After a reaction time of 5 h, the reaction mixture was quenched with 7.92 g of methanol (CH$_3$OH, 0.25 mol, 99.8%, anhydrous, Sigma-Aldrich Chemie GmbH, Taufkirchen, Germany; catalog #322415) and was analyzed via off-line $^1$H NMR (JEOL ECX 400 MHz). $^1$H qNMR analysis of the reaction mixture gave a 2-BrPA yield of about 24 mol % and selectivity of more than about 90 mol %.

Example 22—2-BrPA Synthesis at 100° C. from Lactic Acid with [MIMBS]Br Molten Salt Catalyst, No Water Added, and No Readjustment of the HBr Amount 16.370 g of solid MIMBS (75 mmol, *J. Mater. Chem.*, 2001, 11, 1057-1062), 12.642 g of 48 wt % hydrobromic acid (HBr; 75 mmol, 48%; Sigma-Aldrich Chemie GmbH, Taufkirchen, Germany; catalog #244260), and 64 g of cyclohexane (C$_6$H$_{12}$, 0.76 mol, >99.5%, Sigma-Aldrich Chemie GmbH, Taufkirchen, Germany; catalog #33117) were mixed at room temperature and atmospheric conditions in a 100 mL three-necked glass reactor to produce a biphasic reaction mixture, which was then heated to a temperature of 69.8° C. under continuous stirring with a magnetic stirring bar at a speed of 600 rpm. The protic and HBr loaded ionic liquid [MIMBS]Br was isolated by removing the water using a Dean-Stark-apparatus with external heating to 100° C. and finally decanting the cyclohexane phase after the glass reactor was cooled down to room temperature. 2.559 g of an 88 wt % L-lactic acid solution (25 mmol; Corbion Purac Co., Lenexa, Kans.) were added to the reactor and the activated reaction mixture was heated to 100° C. under continuous stirring with an overhead stirrer at a speed of 600 rpm. The reaction mixture was batchwise refluxed and gaseous by-products were routed to the off-gas or collected in a hydrostatic column. After a reaction time of 5 h, the reaction mixture was quenched with 7.92 g of methanol (CH$_3$OH, 0.25 mol, 99.8%, anhydrous, Sigma-Aldrich Chemie GmbH, Taufkirchen, Germany; catalog #322415) and was analyzed via off-line $^1$H NMR (JEOL ECX 400 MHz). $^1$H qNMR analysis of the reaction mixture gave a 2-BrPA yield of about 8 mol % and selectivity of more than about 90 mol %.

Tabulated results from Examples 17 to 22 can be seen in Table 4 below, where [MIMBS]Br was the PIL used.

TABLE 4

| Example # | Feed Material | Additional Water or HBr? | Reaction Time, [h] | Reaction Temp., [° C.] | 2-BrPAY, [mol %] | 2-BrPAS, [mol %] |
|---|---|---|---|---|---|---|
| 17 | Lactide | no water; no HBr | 5 | 140 | 25 | 77 |
| 18 | Lactide | no water; no HBr | 5 | 120 | 32 | >90 |
| 19 | Lactide | no water; no HBr | 5 | 100 | 16 | >90 |
| 20 | Lactic Acid | no water; no HBr | 5 | 140 | 32 | 74 |
| 21 | Lactic Acid | no water; no HBr | 5 | 120 | 24 | >90 |
| 22 | Lactic Acid | no water; no HBr | 5 | 100 | 8 | >90 |

Comparative Example 23—2-BrPA Synthesis from Lactide at 100° C. with HBr Aqueous Solution and Reaction Time of 24 h 7.21 g of solid lactide (0.05 mol, L,L lactide, polymer grade, Corbion Purac Co., Lenexa, Kans.) were mixed with 50.57 g of 48 wt % hydrobromic acid (HBr; 0.3 mol, 48%; Sigma-Aldrich Chemie GmbH, Taufkirchen, Germany; catalog #244260) in a 100 mL three-necked glass reactor in said molar ratio of 1:3 at room temperature and atmospheric conditions. The reaction mixture was heated to 100° C. under continuous stirring with a magnetic stirring bar at a speed of 300 rpm.

The reaction mixture was batchwise refluxed and gaseous by-products were routed to the off-gas or collected in a hydrostatic column. After a reaction time of 24 hours, the hot solution was allowed to cool down to RT. The aqueous reaction phase was analyzed via off-line $^1$H NMR (JEOL ECX 400 MHz). $^1$H qNMR analysis of the reaction mixture gave a 2-BrPA yield of about 13 mol % and selectivity of about 54 mol %.

Comparative Example 24—2-BrPA Synthesis from Lactide at 100° C. with HBr Aqueous Solution and Reaction Time of 72 h 7.21 g of solid lactide (0.05 mol, L,L lactide, polymer grade, Corbion Purac Co., Lenexa, Kans.) were mixed with 50.57 g of 48 wt % hydrobromic acid (HBr; 0.3 mol, 48%; Sigma-Aldrich Chemie GmbH, Taufkirchen, Germany; catalog #244260) in a 100 mL three-necked glass reactor in said molar ratio of 1:3 at room temperature and atmospheric conditions. The reaction mixture was heated to 100° C. under continuous stirring with a magnetic stirring bar at a speed of 300 rpm. The reaction mixture was batchwise refluxed and gaseous by-products were routed to the off-gas or collected in a hydrostatic column. After a reaction time of 72 hours, the hot solution was allowed to cool down to RT. The aqueous reaction phase was analyzed via off-line $^1$H NMR (JEOL ECX 400 MHz). $^1$H qNMR analysis of the reaction mixture gave a 2-BrPA yield of about 19 mol % and selectivity of about 38 mol %.

Comparative Example 25—2-BrPA Synthesis from Lactide at 90° C. with HBr Aqueous Solution and Reaction Time of 24 h 7.21 g of solid lactide (0.05 mol, L,L lactide, polymer grade, Corbion Purac Co., Lenexa, Kans.) were mixed with 50.57 g of 48 wt % hydrobromic acid (HBr; 0.3 mol, 48%; Sigma-Aldrich Chemie GmbH, Taufkirchen, Germany; catalog #244260) in a 100 mL three-necked glass reactor in said molar ratio of 1:3 at room temperature and atmospheric conditions. The reaction mixture was heated to 90° C. under continuous stirring with a magnetic stirring bar at a speed of 300 rpm. The reaction mixture was batchwise refluxed and gaseous by-products were routed to the off-gas or collected in a hydrostatic column. After a reaction time of 24 hours, the hot solution was allowed to cool down to RT. The aqueous reaction phase was analyzed via off-line $^1$H NMR (JEOL ECX 400 MHz). $^1$H qNMR analysis of the reaction mixture gave a 2-BrPA yield of about 5 mol % and selectivity of about 71 mol %.

Comparative Example 26—2-BrPA Synthesis from Lactide at 120° C. with HBr Aqueous Solution and Reaction Time of 24 h 7.21 g of solid lactide (0.05 mol, L,L lactide, polymer grade, Corbion Purac Co., Lenexa, Kans.) were mixed with 50.57 g of 48 wt % hydrobromic acid (HBr; 0.3 mol, 48%; Sigma-Aldrich Chemie GmbH, Taufkirchen, Germany; catalog #244260) in a 100 mL three-necked glass reactor in said molar ratio of 1:3 at room temperature and atmospheric conditions. The reaction mixture was heated to 120° C. under continuous stirring with a magnetic stirring bar at a speed of 300 rpm. The reaction mixture was batchwise refluxed and gaseous by-products were routed to the off-gas or collected in a hydrostatic column. After a reaction time of 24 hours, the hot solution was allowed to cool down to RT. The aqueous reaction phase was analyzed via off-line $^1$H NMR (JEOL ECX 400 MHz). $^1$H qNMR analysis of the reaction mixture gave a 2-BrPA yield of about 27 mol % and selectivity of about 40 mol %.

Comparative Example 27—2-BrPA Synthesis from Lactide at 100° C. with [PBu$_4$]Br and HBr Molten Salt Catalyst, and Reaction Time of 72 h 7.21 g of solid lactide (0.05 mol, L,L lactide, polymer grade, Corbion Purac Co., Lenexa, Kans.) were mixed with 16.86 g of 48 wt % hydrobromic acid (HBr; 0.1 mmol, 48%; Sigma-Aldrich Chemie GmbH, Taufkirchen, Germany; catalog #244260) and 34.63 g of solid tetrabutylphosphonium bromide ([PBu$_4$]Br; 0.1 mmol, 98%; Sigma-Aldrich Chemie GmbH, Taufkirchen, Germany; catalog #189138) in a 100 mL three-necked glass reactor, at room temperature and atmospheric conditions, and in a molar ratio of lactic acid equivalent (LAe) to HBr to [PBu$_4$]Br equal to 1:1:1. The reaction mixture was heated to 100° C. under continuous stirring with a magnetic stirring bar at a speed of 300 rpm. The reaction mixture was batchwise refluxed and gaseous by-products were routed to the off-gas or collected in a hydrostatic column. After a reaction time of 72 h, the hot solution was allowed to cool down to room. The molten salt phase was analyzed via off-line $^1$H NMR (JEOL ECX 400 MHz). $^1$H qNMR analysis of the reaction mixture gave a 2-BrPA yield of about 21 mol % and selectivity of about 46 mol %.

Comparative Example 28—2-BrPA Synthesis from Lactic Acid at 113° C. with HBr and Chlorobenzene Extraction Phase, and Reaction Time of 24 h 10.24 g of an 88 wt % L-lactic acid solution (0.1 mol, Corbion Purac Co., Lenexa, Kans.) were mixed with 50.57 g of 48 wt % hydrobromic acid (HBr; 0.3 mol, 48%; Sigma-Aldrich Chemie GmbH, Taufkirchen, Germany; catalog #244260) in a 250 mL three-necked glass reactor at room temperature and atmospheric conditions. 33.70 g of chlorobenzene (0.3 mol, anhydrous, 99.8%, Sigma-Aldrich Chemie GmbH, Taufkirchen, Germany; catalog #284513) were added to isolate the formed product. The biphasic reaction mixture was heated to 113° C. under continuous stirring with a magnetic stirring bar at a speed of 300 rpm. The biphasic reaction mixture was batchwise refluxed and gaseous by-products were routed to the off-gas or collected in a hydrostatic column. After a reaction time of 24 h, the hot solution was allowed to cool down to room temperature and the two phases were separated with a separating funnel. The aqueous reaction phase, as well as the organic extraction phase, were both analyzed via off-line $^1$H NMR (JEOL ECX 400 MHz). $^1$H qNMR analysis of the reaction mixture gave a 2-BrPA yield of about 28 mol % and selectivity of about 54 mol %. Similar experiments with: a) toluene produced 2-BrPA yield of about 12 mol % and selectivity of about 65 mol % at 100° C.; and b) bromobenzene produced 2-BrPA yield of about 29 mol % and selectivity of about 40 mol % at 120° C.

Example 29—3-BrPA and Acrylic Acid Synthesis from 2-BrPA with [PBu$_4$]Br Molten Salt Catalyst, Molar Ratio of [PBu$_4$]Br to 2-BrPA 1:1, Temperature 120° C., and Reaction Time 20 h 46.23 g of solid tetrabutylphosphonium bromide ([PBu$_4$]Br; 133.5 mmol, 98%; Sigma-Aldrich Chemie GmbH, Taufkirchen, Germany; catalog #189138) were mixed with 20.68 g of liquid 2-BrPA (133.5 mmol, 99%; Sigma-Aldrich Chemie GmbH, Taufkirchen, Germany; catalog # B78300) in a 100 mL three-necked glass reactor in a molar ratio of 1:1 at room temperature and atmospheric conditions. The isomerization mixture was heated to 120° C. under continuous stirring with a magnetic stirring bar at a speed of 450 rpm. The isomerization mixture was batchwise refluxed and gaseous by-products were routed to the off-gas or collected in a hydrostatic column. After a reaction time of 20 h, the hot reaction mixture was allowed to cool down to room temperature and was analyzed via off-line $^1$H NMR (JEOL ECX 400 MHz). $^1$H qNMR analysis of the isomerization mixture gave a 3-BrPA yield of about 36 mol % and selectivity of about 71 mol %, acrylic acid yield of about 2 mol %, and 2-BrPA conversion of about 51 mol %.

Example 30—3-BrPA and Acrylic Acid Synthesis from 2-BrPA with [PBu$_4$]Br Molten Salt Catalyst, Molar Ratio of [PBu$_4$]Br to 2-BrPA 1:1, Temperature 140° C., and Reaction Time 20 h 46.23 g of solid tetrabutylphosphonium bromide ([PBu$_4$]Br; 133.5 mmol, 98%; Sigma-Aldrich Chemie GmbH, Taufkirchen, Germany; catalog #189138) were mixed with 20.68 g of liquid 2-BrPA (133.5 mmol, 99%; Sigma-Aldrich Chemie GmbH, Taufkirchen, Germany; catalog # B78300) in a 100 mL three-necked glass reactor in a molar ratio of 1:1 at room temperature and atmospheric conditions. The isomerization mixture was heated to 140° C. under continuous stirring with a magnetic stirring bar at a speed of 450 rpm. The isomerization mixture was batchwise refluxed and gaseous by-products were routed to the off-gas or collected in a hydrostatic column. After a reaction time of 20 h, the hot reaction mixture was allowed to cool down to room temperature and was analyzed via off-line $^1$H NMR (JEOL ECX 400 MHz). $^1$H qNMR analysis of the isomerization mixture gave a 3-BrPA yield of about 30 mol % and selectivity of about 59 mol %, acrylic acid yield of about 2 mol %, and 2-BrPA conversion of about 51 mol %.

Example 31—3-BrPA and Acrylic Acid Synthesis from 2-BrPA with [PBu$_4$]Br Molten Salt Catalyst, Molar Ratio of [PBu$_4$]Br to 2-BrPA 1:1, Temperature 160° C., and Reaction Time 20 h 46.23 g of solid tetrabutylphosphonium bromide ([PBu$_4$]Br; 133.5 mmol, 98%; Sigma-Aldrich Chemie GmbH, Taufkirchen, Germany; catalog #189138) were mixed with 20.68 g of liquid 2-BrPA (133.5 mmol, 99%; Sigma-Aldrich Chemie GmbH, Taufkirchen, Germany; catalog # B78300) in a 100 mL three-necked glass reactor in a molar ratio of 1:1 at room temperature and atmospheric conditions. The isomerization mixture was heated to 160° C. under continuous stirring with a magnetic stirring bar at a speed of 450 rpm. The isomerization mixture was batchwise refluxed and gaseous by-products were routed to the off-gas or collected in a hydrostatic column. After a reaction time of 20 h, the hot reaction mixture was allowed to cool down to room temperature and was analyzed via off-line $^1$H NMR (JEOL ECX 400 MHz). $^1$H qNMR analysis of the isomerization mixture gave a 3-BrPA yield of about 79 mol % and selectivity of about 89 mol %, acrylic acid yield of about 3 mol %, and 2-BrPA conversion of about 89 mol %.

Example 32—3-BrPA and Acrylic Acid Synthesis from 2-BrPA with [PBu$_4$]Br Molten Salt Catalyst, Molar Ratio of [PBu$_4$]Br to 2-BrPA 1:1, Temperature 180° C., and Reaction Time 20 h 46.23 g of solid tetrabutylphosphonium bromide ([PBu$_4$]Br; 133.5 mmol, 98%; Sigma-Aldrich Chemie GmbH, Taufkirchen, Germany; catalog #189138) were mixed with 20.68 g of liquid 2-BrPA (133.5 mmol, 99%; Sigma-Aldrich Chemie GmbH, Taufkirchen, Germany; catalog # B78300) in a 100 mL three-necked glass reactor in a molar ratio of 1:1 at room temperature and atmospheric conditions. The isomerization mixture was heated to 180° C. under continuous stirring with a magnetic stirring bar at a speed of 450 rpm. The isomerization mixture was batchwise refluxed and gaseous by-products were routed to the off-gas or collected in a hydrostatic column. After a reaction time of 20 h, the hot reaction mixture was allowed to cool down to room temperature and was analyzed via off-line $^1$H NMR (JEOL ECX 400 MHz). $^1$H qNMR analysis of the isomerization mixture gave a 3-BrPA yield of about 62 mol % and selectivity of about 67 mol %, acrylic acid yield of about 1 mol %, and 2-BrPA conversion of about 92 mol %.

Example 33—3-BrPA and Acrylic Acid Synthesis from 2-BrPA with [PBu$_4$]Br Molten Salt Catalyst, Molar Ratio of [PBu$_4$]Br to 2-BrPA 1:1, Temperature 160° C., and Reaction Time 3 h 46.23 g of solid tetrabutylphosphonium bromide ([PBu$_4$]Br; 133.5 mmol, 98%; Sigma-Aldrich Chemie GmbH, Taufkirchen, Germany; catalog #189138) were mixed with 20.68 g of liquid 2-BrPA (133.5 mmol, 99%; Sigma-Aldrich Chemie GmbH, Taufkirchen, Germany; catalog # B78300) in a 100 mL three-necked glass reactor in a molar ratio of 1:1 at room temperature and atmospheric conditions. The isomerization mixture was heated to 160° C. under continuous stirring with a magnetic stirring bar at a speed of 450 rpm. The isomerization mixture was batchwise refluxed and gaseous by-products were routed to the off-gas or collected in a hydrostatic column. After a reaction time of 3 h, the hot reaction mixture was allowed to cool down to room temperature and was analyzed via off-line $^1$H NMR (JEOL ECX 400 MHz). $^1$H qNMR analysis of the isomerization mixture gave a 3-BrPA yield of about 25 mol % and selectivity of about 57 mol %, acrylic acid yield of about 2 mol %, and 2-BrPA conversion of about 44 mol %.

Example 34—3-BrPA and Acrylic Acid Synthesis from 2-BrPA with [PBu$_4$]Br Molten Salt Catalyst, Molar Ratio of [PBu$_4$]Br to 2-BrPA 9:1, Temperature 160° C., and Reaction Time 1 h 46.23 g of solid tetrabutylphosphonium bromide ([PBu$_4$]Br; 133.5 mmol, 98%; Sigma-Aldrich Chemie GmbH, Taufkirchen, Germany; catalog #189138) were mixed with 2.29 g of liquid 2-BrPA (14.9 mmol, 99%; Sigma-Aldrich Chemie GmbH, Taufkirchen, Germany; catalog # B78300) in a 100 mL three-necked glass reactor in a molar ratio of 9:1 at room temperature and atmospheric conditions. The isomerization mixture was heated to 160° C. under continuous stirring with a magnetic stirring bar at a speed of 450 rpm. The isomerization mixture was batchwise refluxed and gaseous by-products were routed to the off-gas or collected in a hydrostatic column. After a reaction time of 1 h, the hot reaction mixture was allowed to cool down to room temperature and was analyzed via off-line $^1$H NMR (JEOL ECX 400 MHz). $^1$H qNMR analysis of the isomerization mixture gave a 3-BrPA yield of about 19 mol % and selectivity of about 28 mol %, acrylic acid yield of about 32 mol %, and 2-BrPA conversion of about 67 mol %.

Example 35—3-BrPA and Acrylic Acid Synthesis from 2-BrPA with [PBu$_4$]Br Molten Salt Catalyst, Molar Ratio of [PBu$_4$]Br to 2-BrPA 9:1, Temperature 160° C., and Reaction Time 2 h 46.23 g of solid tetrabutylphosphonium bromide ([PBu$_4$]Br; 133.5 mmol, 98%; Sigma-Aldrich Chemie GmbH, Taufkirchen, Germany; catalog #189138) were mixed with 2.29 g of liquid 2-BrPA (14.9 mmol, 99%; Sigma-Aldrich Chemie GmbH, Taufkirchen, Germany; catalog # B78300) in a 100 mL three-necked glass reactor in a molar ratio of 9:1 at room temperature and atmospheric conditions. The isomerization mixture was heated to 160° C. under continuous stirring with a magnetic stirring bar at a speed of 450 rpm. The isomerization mixture was batchwise refluxed and gaseous by-products were routed to the off-gas or collected in a hydrostatic column. After a reaction time of 2 h, the hot reaction mixture was allowed to cool down to room temperature and was analyzed via off-line $^1$H NMR (JEOL ECX 400 MHz). $^1$H qNMR analysis of the isomerization mixture gave a 3-BrPA yield of about 26 mol % and selectivity of about 32 mol %, acrylic acid yield of about 41 mol %, and 2-BrPA conversion of about 81 mol %.

Example 36—3-BrPA and Acrylic Acid Synthesis from 2-BrPA with [PBu$_4$]Br Molten Salt Catalyst, Molar Ratio of [PBu$_4$]Br to 2-BrPA 9:1, Temperature 160° C., and Reaction Time 3 h 46.23 g of solid tetrabutylphosphonium bromide ([PBu$_4$]Br; 133.5 mmol, 98%; Sigma-Aldrich Chemie GmbH, Taufkirchen, Germany; catalog #189138) were mixed with 2.29 g of liquid 2-BrPA (14.9 mmol, 99%; Sigma-Aldrich Chemie GmbH, Taufkirchen, Germany; catalog # B78300) in a 100 mL three-necked glass reactor in a molar ratio of 9:1 at room temperature and atmospheric conditions. The isomerization mixture was heated to 160° C. under continuous stirring with a magnetic stirring bar at a speed of 450 rpm. The isomerization mixture was batchwise refluxed and gaseous by-products were routed to the off-gas or collected in a hydrostatic column. After a reaction time of 3 h, the hot reaction mixture was allowed to cool down to room temperature and was analyzed via off-line $^1$H NMR (JEOL ECX 400 MHz). $^1$H qNMR analysis of the isomerization mixture gave a 3-BrPA yield of about 29 mol % and selectivity of about 33 mol %, acrylic acid yield of about 47 mol %, and 2-BrPA conversion of about 87 mol %.

Example 37—3-BrPA and Acrylic Acid Synthesis from 2-BrPA with [PBu$_4$]Br Molten Salt Catalyst, Molar Ratio of [PBu$_4$]Br to 2-BrPA 9:1, Temperature 160° C., and Reaction Time 4 h 46.23 g of solid tetrabutylphosphonium bromide ([PBu$_4$]Br; 133.5 mmol, 98%; Sigma-Aldrich Chemie GmbH, Taufkirchen, Germany; catalog #189138) were mixed with 2.29 g of liquid 2-BrPA (14.9 mmol, 99%; Sigma-Aldrich Chemie GmbH, Taufkirchen, Germany; catalog # B78300) in a 100 mL three-necked glass reactor in a molar ratio of 9:1 at room temperature and atmospheric conditions. The isomerization mixture was heated to 160° C. under continuous stirring with a magnetic stirring bar at a speed of 450 rpm. The isomerization mixture was batchwise refluxed and gaseous by-products were routed to the off-gas or collected in a hydrostatic column. After a reaction time of 4 h, the hot reaction mixture was allowed to cool down to room temperature and was analyzed via off-line $^1$H NMR (JEOL ECX 400 MHz). $^1$H qNMR analysis of the isomerization mixture gave a 3-BrPA yield of about 30 mol % and selectivity of about 34 mol %, acrylic acid yield of about 47 mol %, and 2-BrPA conversion of about 88 mol %.

Example 38—3-BrPA and Acrylic Acid Synthesis from 2-BrPA with [PBu$_4$]Br Molten Salt Catalyst, Molar Ratio of [PBu$_4$]Br to 2-BrPA 9:1, Temperature 160° C., and Reaction Time 6 h 46.23 g of solid tetrabutylphosphonium bromide ([PBu$_4$]Br; 133.5 mmol, 98%; Sigma-Aldrich Chemie GmbH, Taufkirchen, Germany; catalog #189138) were mixed with 2.29 g of liquid 2-BrPA (14.9 mmol, 99%; Sigma-Aldrich Chemie GmbH, Taufkirchen, Germany; catalog # B78300) in a 100 mL three-necked glass reactor in a molar ratio of 9:1 at room temperature and atmospheric conditions. The isomerization mixture was heated to 160° C. under continuous stirring with a magnetic stirring bar at a speed of 450 rpm. The isomerization mixture was batchwise refluxed and gaseous by-products were routed to the off-gas or collected in a hydrostatic column. After a reaction time of 6 h, the hot reaction mixture was allowed to cool down to room temperature and was analyzed via off-line $^1$H NMR (JEOL ECX 400 MHz). $^1$H qNMR analysis of the isomerization mixture gave a 3-BrPA yield of about 33 mol % and selectivity of about 34 mol %, acrylic acid yield of about 47 mol %, and 2-BrPA conversion of about 96 mol %.

Example 39—3-BrPA and acrylic acid synthesis from 2-BrPA with [PBu$_4$]Br molten salt catalyst, molar ratio of [PBu$_4$]Br to 2-BrPA 9:1, temperature 100° C., and reaction time 3 h 46.23 g of solid tetrabutylphosphonium bromide ([PBu$_4$]Br; 133.5 mmol, 98%; Sigma-Aldrich Chemie GmbH, Taufkirchen, Germany; catalog #189138) were mixed with 2.29 g of liquid 2-BrPA (14.9 mmol, 99%; Sigma-Aldrich Chemie GmbH, Taufkirchen, Germany; catalog # B78300) in a 100 mL three-necked glass reactor in a molar ratio of 9:1 at room temperature and atmospheric conditions. The isomerization mixture was heated to 100° C. under continuous stirring with a magnetic stirring bar at a speed of 450 rpm. The isomerization mixture was batchwise refluxed and gaseous by-products were routed to the off-gas or collected in a hydrostatic column. After a reaction time of 3 h, the hot reaction mixture was allowed to cool down to room temperature and was analyzed via off-line $^1$H NMR (JEOL ECX 400 MHz). $^1$H qNMR analysis of the isomerization mixture gave no 3-BrPA, no acrylic acid, and 2-BrPA conversion of about 14 mol %.

Example 40—3-BrPA and Acrylic Acid Synthesis from 2-BrPA with [PBu$_4$]Br Molten Salt Catalyst, Molar Ratio of [PBu$_4$]Br to 2-BrPA 9:1, Temperature 120° C., and Reaction Time 3 h 46.23 g of solid tetrabutylphosphonium bromide ([PBu$_4$]Br; 133.5 mmol, 98%; Sigma-Aldrich Chemie GmbH, Taufkirchen, Germany; catalog #189138) were mixed with 2.29 g of liquid 2-BrPA (14.9 mmol, 99%; Sigma-Aldrich Chemie GmbH, Taufkirchen, Germany; catalog # B78300) in a 100 mL three-necked glass reactor in a molar ratio of 9:1 at room temperature and atmospheric conditions. The isomerization mixture was heated to 120° C. under continuous stirring with a magnetic stirring bar at a speed of 450 rpm. The isomerization mixture was batchwise refluxed and gaseous by-products were routed to the off-gas or collected in a hydrostatic column. After a reaction time of 3 h, the hot reaction mixture was allowed to cool down to room temperature and was analyzed via off-line $^1$H NMR (JEOL ECX 400 MHz). $^1$H qNMR analysis of the isomerization mixture gave 3-BrPA yield of about 4 mol % and selectivity of about 15 mol %, acrylic acid yield of about 17 mol %, and 2-BrPA conversion of about 26 mol %.

Example 41—3-BrPA and Acrylic Acid Synthesis from 2-BrPA with [PBu$_4$]Br Molten Salt Catalyst, Molar Ratio of [PBu$_4$]Br to 2-BrPA 9:1, Temperature 140° C., and Reaction Time 3 h 46.23 g of solid tetrabutylphosphonium bromide ([PBu$_4$]Br; 133.5 mmol, 98%; Sigma-Aldrich Chemie GmbH, Taufkirchen, Germany; catalog #189138) were mixed with 2.29 g of liquid 2-BrPA (14.9 mmol, 99%; Sigma-Aldrich Chemie GmbH, Taufkirchen, Germany; catalog # B78300) in a 100 mL three-necked glass reactor in a molar ratio of 9:1 at room temperature and atmospheric conditions. The isomerization mixture was heated to 140° C. under continuous stirring with a magnetic stirring bar at a speed of 450 rpm. The isomerization mixture was batchwise refluxed and gaseous by-products were routed to the off-gas or collected in a hydrostatic column.

After a reaction time of 3 h, the hot reaction mixture was allowed to cool down to room temperature and was analyzed via off-line $^1$H NMR (JEOL ECX 400 MHz). $^1$H qNMR analysis of the isomerization mixture gave 3-BrPA yield of about 15 mol % and selectivity of about 28 mol %, acrylic acid yield of about 20 mol %, and 2-BrPA conversion of about 53 mol %.

Example 42—3-BrPA and Acrylic Acid Synthesis from 2-BrPA with [PBu$_4$]Br Molten Salt Catalyst, Molar Ratio of [PBu$_4$]Br to 2-BrPA 9:1, Temperature 180° C., and Reaction Time 3 h 46.23 g of solid tetrabutylphosphonium bromide ([PBu$_4$]Br; 133.5 mmol, 98%; Sigma-Aldrich Chemie GmbH, Taufkirchen, Germany; catalog #189138) were mixed with 2.29 g of liquid 2-BrPA (14.9 mmol, 99%; Sigma-Aldrich Chemie GmbH, Taufkirchen, Germany; catalog # B78300) in a 100 mL three-necked glass reactor in a molar ratio of 9:1 at room temperature and atmospheric conditions. The isomerization mixture was heated to 180° C. under continuous stirring with a magnetic stirring bar at a speed of 450 rpm. The isomerization mixture was batchwise refluxed and gaseous by-products were routed to the off-gas or collected in a hydrostatic column. After a reaction time of 3 h, the hot reaction mixture was allowed to cool down to room temperature and was analyzed via off-line $^1$H NMR (JEOL ECX 400 MHz). $^1$H qNMR analysis of the isomerization mixture gave 3-BrPA yield of about 52 mol % and selectivity of about 54 mol %, acrylic acid yield of about 45 mol %, and 2-BrPA conversion of about 97 mol %.

Example 43—3-BrPA and Acrylic Acid Synthesis from 2-BrPA with [PBu$_4$]Br Molten Salt Catalyst, Molar Ratio of [PBu$_4$]Br to 2-BrPA 1:3, Temperature 160° C., and Reaction Time 3 h 15.41 g of solid tetrabutylphosphonium bromide ([PBu$_4$]Br; 44.5 mmol, 98%; Sigma-Aldrich Chemie GmbH, Taufkirchen, Germany; catalog #189138) were mixed with 20.68 g of liquid 2-BrPA (133.5 mmol, 99%; Sigma-Aldrich Chemie GmbH, Taufkirchen, Germany; catalog # B78300) in a 100 mL three-necked glass reactor in a molar ratio of 1:3 at room temperature and atmospheric conditions. The isomerization mixture was heated to 160° C. under continuous stirring with a magnetic stirring bar at a speed of 450 rpm. The isomerization mixture was batchwise refluxed and gaseous by-products were routed to the off-gas or collected in a hydrostatic column. After a reaction time of 3 h, the hot reaction mixture was allowed to cool down to room temperature and was analyzed via off-line $^1$H NMR (JEOL ECX 400 MHz). $^1$H qNMR analysis of the isomerization mixture gave a 3-BrPA yield of about 4 mol % and selectivity of about 19 mol %, no acrylic acid, and 2-BrPA conversion of about 21 mol %.

Example 44—3-BrPA and Acrylic Acid Synthesis from 2-BrPA with [PBu$_4$]Br Molten Salt Catalyst, Molar Ratio of [PBu$_4$]Br to 2-BrPA 3:1, Temperature 160° C., and Reaction Time 3 h 46.23 g of solid tetrabutylphosphonium bromide ([PBu$_4$]Br; 133.5 mmol, 98%; Sigma-Aldrich Chemie GmbH, Taufkirchen, Germany; catalog #189138) were mixed with 6.89 g of liquid 2-BrPA (44.1 mmol, 99%; Sigma-Aldrich Chemie GmbH, Taufkirchen, Germany; catalog # B78300) in a 100 mL three-necked glass reactor in a molar ratio of 3:1 at room temperature and atmospheric conditions. The isomerization mixture was heated to 160° C. under continuous stirring with a magnetic stirring bar at a speed of 450 rpm. The isomerization mixture was batchwise refluxed and gaseous by-products were routed to the off-gas or collected in a hydrostatic column. After a reaction time of 3 h, the hot reaction mixture was allowed to cool down to room temperature and was analyzed via off-line $^1$H NMR (JEOL ECX 400 MHz). $^1$H qNMR analysis of the isomerization mixture gave a 3-BrPA yield of about 38 mol % and selectivity of about 49 mol %, acrylic acid yield of about 23 mol %, and 2-BrPA conversion of about 78 mol %.

Example 45—3-BrPA and Acrylic Acid Synthesis from 2-BrPA with [PBu$_4$]Br Molten Salt Catalyst, Molar Ratio of [PBu$_4$]Br to 2-BrPA 6:1, Temperature 160° C., and Reaction Time 3 h 46.23 g of solid tetrabutylphosphonium bromide ([PBu$_4$]Br; 133.5 mmol, 98%; Sigma-Aldrich Chemie GmbH, Taufkirchen, Germany; catalog #189138) were mixed with 3.45 g of liquid 2-BrPA (22.1 mmol, 99%; Sigma-Aldrich Chemie GmbH, Taufkirchen, Germany; catalog # B78300) in a 100 mL three-necked glass reactor in a molar ratio of 6:1 at room temperature and atmospheric conditions. The isomerization mixture was heated to 160° C. under continuous stirring with a magnetic stirring bar at a speed of 450 rpm. The isomerization mixture was batchwise refluxed and gaseous by-products were routed to the off-gas or collected in a hydrostatic column.

After a reaction time of 3 h, the hot reaction mixture was allowed to cool down to room temperature and was analyzed via off-line $^1$H NMR (JEOL ECX 400 MHz). $^1$H qNMR analysis of the isomerization mixture gave a 3-BrPA yield of about 39 mol % and selectivity of about 46 mol %, acrylic acid yield of about 31 mol %, and 2-BrPA conversion of about 85 mol %.

Example 46—3-BrPA and Acrylic Acid Synthesis from 2-BrPA with [PBu$_4$]Br Molten Salt Catalyst, Molar Ratio of [PBu$_4$]Br to 2-BrPA 12:1, Temperature 160° C., and Reaction Time 3 h 46.23 g of solid tetrabutylphosphonium bromide ([PBu$_4$]Br; 133.5 mmol, 98%; Sigma-Aldrich Chemie GmbH, Taufkirchen, Germany; catalog #189138) were mixed with 1.72 g of liquid 2-BrPA (11.1 mmol, 99%; Sigma-Aldrich Chemie GmbH, Taufkirchen, Germany; catalog # B78300) in a 100 mL three-necked glass reactor in a molar ratio of 12:1 at room temperature and atmospheric conditions. The isomerization mixture was heated to 160° C. under continuous stirring with a magnetic stirring bar at a speed of 450 rpm. The isomerization mixture was batchwise refluxed and gaseous by-products were routed to the off-gas or collected in a hydrostatic column. After a reaction time of 3 h, the hot reaction mixture was allowed to cool down to room temperature and was analyzed via off-line $^1$H NMR (JEOL ECX 400 MHz). $^1$H qNMR analysis of the isomerization mixture gave a 3-BrPA yield of about 28 mol % and selectivity of about 31 mol %, acrylic acid yield of about 41 mol %, and 2-BrPA conversion of about 89 mol %.

Example 47—3-BrPA and Acrylic Acid Synthesis from 2-BrPA with [PBu₄]Br Molten Salt Catalyst, Molar Ratio of [PBu₄]Br to 2-BrPA 15:1, Temperature 160° C., and Reaction Time 3 h 46.23 g of solid tetrabutylphosphonium bromide ([PBu₄]Br; 133.5 mmol, 98%; Sigma-Aldrich Chemie GmbH, Taufkirchen, Germany; catalog #189138) were mixed with 1.37 g of liquid 2-BrPA (8.8 mmol, 99%; Sigma-Aldrich Chemie GmbH, Taufkirchen, Germany; catalog #B78300) in a 100 mL three-necked glass reactor in a molar ratio of 15:1 at room temperature and atmospheric conditions. The isomerization mixture was heated to 160° C. under continuous stirring with a magnetic stirring bar at a speed of 450 rpm. The isomerization mixture was batchwise refluxed and gaseous by-products were routed to the off-gas or collected in a hydrostatic column. After a reaction time of 3 h, the hot reaction mixture was allowed to cool down to room temperature and was analyzed via off-line ¹H NMR (JEOL ECX 400 MHz). ¹H qNMR analysis of the isomerization mixture gave a 3-BrPA yield of about 23 mol % and selectivity of about 26 mol %, acrylic acid yield of about 50 mol %, and 2-BrPA conversion of about 87 mol %.

Example 48—3-BrPA and Acrylic Acid Synthesis from 2-BrPA with [PBu₄]Br Molten Salt Catalyst, Molar Ratio of [PBu₄]Br to 2-BrPA 18:1, Temperature 160° C., and Reaction Time 3 h 46.23 g of solid tetrabutylphosphonium bromide ([PBu₄]Br; 133.5 mmol, 98%; Sigma-Aldrich Chemie GmbH, Taufkirchen, Germany; catalog #189138) were mixed with 1.14 g of liquid 2-BrPA (7.4 mmol, 99%; Sigma-Aldrich Chemie GmbH, Taufkirchen, Germany; catalog #B78300) in a 100 mL three-necked glass reactor in a molar ratio of 18:1 at room temperature and atmospheric conditions. The isomerization mixture was heated to 160° C. under continuous stirring with a magnetic stirring bar at a speed of 450 rpm. The isomerization mixture was batchwise refluxed and gaseous by-products were routed to the off-gas or collected in a hydrostatic column. After a reaction time of 3 h, the hot reaction mixture was allowed to cool down to room temperature and was analyzed via off-line ¹H NMR (JEOL ECX 400 MHz). ¹H qNMR analysis of the isomerization mixture gave a 3-BrPA yield of about 22 mol % and selectivity of about 28 mol %, acrylic acid yield of about 54 mol %, and 2-BrPA conversion of about 79 mol %.

Tabulated results from Examples 29 to 48 can be seen in Table 5 below (IL is [PBu₄]Br).

TABLE 5

| Example # | Molar ratio of IL to 2-BrPA, [—] | Reaction Time, [h] | Reaction Temp., [° C.] | 3-BrPAY, [mol %] | AAY, [mol %] | 3-BrPAY + AAY, [mol %] |
|---|---|---|---|---|---|---|
| 29 | 1:1 | 20 | 120 | 36 | 2 | 38 |
| 30 | 1:1 | 20 | 140 | 30 | 2 | 32 |
| 31 | 1:1 | 20 | 160 | 79 | 3 | 82 |
| 32 | 1:1 | 20 | 180 | 62 | 1 | 63 |
| 33 | 1:1 | 3 | 160 | 25 | 2 | 27 |
| 34 | 9:1 | 1 | 160 | 19 | 32 | 51 |
| 35 | 9:1 | 2 | 160 | 26 | 41 | 67 |
| 36 | 9:1 | 3 | 160 | 29 | 47 | 76 |
| 37 | 9:1 | 4 | 160 | 30 | 47 | 77 |
| 38 | 9:1 | 6 | 160 | 33 | 47 | 80 |
| 39 | 9:1 | 3 | 100 | 0 | 0 | 0 |
| 40 | 9:1 | 3 | 120 | 4 | 17 | 21 |
| 41 | 9:1 | 3 | 140 | 15 | 20 | 35 |
| 42 | 9:1 | 3 | 180 | 52 | 45 | 97 |
| 43 | 1:3 | 3 | 160 | 4 | 0 | 4 |
| 44 | 3:1 | 3 | 160 | 38 | 23 | 61 |
| 45 | 6:1 | 3 | 160 | 39 | 31 | 70 |
| 46 | 12:1 | 3 | 160 | 28 | 41 | 69 |
| 47 | 15:1 | 3 | 160 | 23 | 50 | 73 |
| 48 | 18:1 | 3 | 160 | 22 | 54 | 76 |

Example 49—3-BrPA and Acrylic Acid Synthesis from 2-BrPA with [EMIM]Br Molten Salt Catalyst, Molar Ratio of EMIMBr to 2-BrPA 1:1, Temperature 140° C., and Reaction Time 20 h 25 g of solid 1-ethyl-3-methylimidazolium bromide ([EMIM]Br; 130.9 mmol, for synthesis; Merck KGaA, Darmstadt, Germany; catalog #4.90038.0025) were mixed with 20.03 g of liquid 2-BrPA (130.9 mmol, 99%; Sigma-Aldrich Chemie GmbH, Taufkirchen, Germany; catalog # B78300) in a 100 mL three-necked glass reactor in a molar ratio of 1:1 at room temperature and atmospheric conditions. The isomerization mixture was heated to 140° C. under continuous stirring with a magnetic stirring bar at a speed of 450 rpm. The isomerization mixture was batchwise refluxed and gaseous by-products were routed to the off-gas or collected in a hydrostatic column. After a reaction time of 20 h, the hot reaction mixture was analyzed via off-line ¹H NMR (JEOL ECX 400 MHz). ¹H qNMR analysis of the isomerization mixture gave 3-BrPA yield of about 74 mol % and selectivity of about 95 mol %, no acrylic acid, and 2-BrPA conversion of about 78 mol %.

Example 50—3-BrPA and Acrylic Acid Synthesis from 2-BrPA with [1B4MPyr]Br Molten Salt Catalyst, Molar Ratio of [1B4MPyr]Br to 2-BrPA 1:1, Temperature 140° C., and Reaction Time 20 h 29.79 g of solid 1-butyl-4-methylpyridinium bromide ([1B4MPyr]Br; 130 mmol, for synthesis; Merck KGaA, Darmstadt, Germany; catalog #4.90174) were mixed with 20 g of liquid 2-BrPA (130 mmol, 99%; Sigma-Aldrich Chemie GmbH, Taufkirchen, Germany; catalog #B78300) in a 100 mL three-necked glass reactor in a molar ratio of 1:1 at room temperature and atmospheric conditions. The isomerization mixture was heated to 140° C. under continuous stirring with a magnetic stirring bar at a speed of 450 rpm. The isomerization mixture was batchwise refluxed and gaseous by-products were routed to the off-gas or collected in a hydrostatic column. After a reaction time of 20 h, the hot reaction mixture was analyzed via off-line $^1$H NMR (JEOL ECX 400 MHz). $^1$H qNMR analysis of the isomerization mixture gave 3-BrPA yield of about 65 mol % and selectivity of about 93 mol %, acrylic acid yield of about 1 mol %, and 2-BrPA conversion of about 70 mol %.

Example 51—3-BrPA and Acrylic Acid Synthesis from 2-BrPA with [1E1MPyrro]Br Molten Salt Catalyst, Molar Ratio of [1E1MPyrro]Br to 2-BrPA 1:1, Temperature 140° C., and Reaction Time 20 h 22.65 g of solid 1-ethyl-1-methylpyrrolidinium bromide ([1E1MPyrro]Br; 115.5 mmol, 99%; Sigma-Aldrich Chemie GmbH, Taufkirchen, Germany; catalog #713171) were mixed with 18.02 g of liquid 2-BrPA (116.6 mmol, 99%; Sigma-Aldrich Chemie GmbH, Taufkirchen, Germany; catalog # B78300) in a 100 mL three-necked glass reactor in a molar ratio of 1:1 at room temperature and atmospheric conditions. The isomerization mixture was heated to 140° C. under continuous stirring with a magnetic stirring bar at a speed of 450 rpm. The isomerization mixture was batchwise refluxed and gaseous by-products were routed to the off-gas or collected in a hydrostatic column. After a reaction time of 20 h, the hot reaction mixture was analyzed via off-line $^1$H NMR (JEOL ECX 400 MHz). $^1$H qNMR analysis of the isomerization mixture gave 3-BrPA yield of about 69 mol % and selectivity of about 83 mol %, acrylic acid yield of about 2 mol %, and 2-BrPA conversion of about 70 mol %.

Example 52—3-BrPA and Acrylic Acid Synthesis from 2-BrPA with [PPh$_3$Et]Br Molten Salt Catalyst, Molar Ratio of [PPh$_3$Et]Br to 2-BrPA 1:1, Temperature 140° C., and Reaction Time 20 h 24.99 g of solid ethyl triphenylphosphonium bromide ([PPh$_3$Et]Br; 66.3 mmol, 99%; Sigma-Aldrich Chemie GmbH, Taufkirchen, Germany; catalog # E50604) were mixed with 10.28 g of liquid 2-BrPA (66.5 mmol, 99%; Sigma-Aldrich Chemie GmbH, Taufkirchen, Germany; catalog # B78300) in a 100 mL three-necked glass reactor in a molar ratio of 1:1 at room temperature and atmospheric conditions. The isomerization mixture was heated to 140° C. under continuous stirring with a magnetic stirring bar at a speed of 450 rpm. The isomerization mixture was batchwise refluxed and gaseous by-products were routed to the off-gas or collected in a hydrostatic column. After a reaction time of 20 h, the hot reaction mixture was analyzed via off-line $^1$H NMR (JEOL ECX 400 MHz). $^1$H qNMR analysis of the isomerization mixture gave 3-BrPA yield of about 63 mol % and selectivity of about 88 mol %, acrylic acid yield of about 2 mol %, and 2-BrPA conversion of about 72 mol %.

Example 53—3-BrPA and Acrylic Acid Synthesis from 2-BrPA with [PBuPh$_3$]Br Molten Salt Catalyst, Molar Ratio of [PBuPh$_3$]Br to 2-BrPA 1:1, Temperature 140° C., and Reaction Time 20 h 24.76 g of solid butyltriphenylphosphonium bromide ([PBuPh$_3$]Br; 62 mmol; Chem. Commun., 2015, 51(43), 9002-9005) were mixed with 9.56 g of liquid 2-BrPA (62.5 mmol, 99%; Sigma-Aldrich Chemie GmbH, Taufkirchen, Germany; catalog # B78300) in a 100 mL three-necked glass reactor in a molar ratio of 1:1 at room temperature and atmospheric conditions. The isomerization mixture was heated to 140° C. under continuous stirring with a magnetic stirring bar at a speed of 450 rpm. The isomerization mixture was batchwise refluxed and gaseous by-products were routed to the off-gas or collected in a hydrostatic column. After a reaction time of 20 h, the hot reaction mixture was analyzed via off-line $^1$H NMR (JEOL ECX 400 MHz). $^1$H qNMR analysis of the isomerization mixture gave 3-BrPA yield of about 44 mol % and selectivity of about 71 mol %, no acrylic acid, and 2-BrPA conversion of about 62 mol %.

Example 54—3-BrPA and Acrylic Acid Synthesis from 2-BrPA with [PBu$_3$pH]Br Molten Salt Catalyst, Molar Ratio of [PBu$_3$pH]Br to 2-BrPA 1:1, Temperature 140° C., and Reaction Time 20 h 46.23 g of solid tributylphenylphosphonium bromide ([PBu$_3$Ph]Br; 69.66 mmol; Adv. Synth. Catal., 2008, 350 (18), 2967-2974; using tributylphosphine and bromobenzene instead of triphenylphosphine and 4-bromotoluene) were mixed with 10.68 g of liquid 2-BrPA (69.8 mmol, 99%; Sigma-Aldrich Chemie GmbH, Taufkirchen, Germany; catalog # B78300) in a 100 mL three-necked glass reactor in a molar ratio of 1:1 at room temperature and atmospheric conditions. The isomerization mixture was heated to 140° C. under continuous stirring with a magnetic stirring bar at a speed of 450 rpm. The isomerization mixture was batchwise refluxed and gaseous by-products were routed to the off-gas or collected in a hydrostatic column. After a reaction time of 20 h, the hot reaction mixture was analyzed via off-line $^1$H NMR (JEOL ECX 400 MHz). $^1$H qNMR analysis of the isomerization mixture gave 3-BrPA yield of about 28 mol % and selectivity of about 48 mol %, acrylic acid yield of about 1 mol %, and 2-BrPA conversion of about 58 mol %.

Tabulated results from Examples 49 to 54 can be seen in Table 6 below (molar ratio of IL to 2-BrPA is 1:1).

TABLE 6

| Example # | IL, [—] | Reaction Time, [h] | Reaction Temp., [° C.] | 3-BrPAY, [mol %] | AAY, [mol %] | 3-BrPAY + AAY, [mol %] |
| --- | --- | --- | --- | --- | --- | --- |
| 49 | [EMIM]Br | 20 | 140 | 74 | 0 | 74 |
| 50 | [1B4MPyr]Br | 20 | 140 | 65 | 1 | 66 |
| 51 | [1E1MPyrro]Br | 20 | 140 | 69 | 2 | 71 |
| 52 | [PPh$_3$Et]Br | 20 | 140 | 63 | 2 | 65 |
| 53 | [PBuPh$_3$]Br | 20 | 140 | 44 | 0 | 44 |
| 54 | [PBu$_3$Ph]Br | 20 | 140 | 28 | 1 | 29 |

Example 55—Acrylic Acid Synthesis from 3-BrPA with Trioctylamine (TOA) at Temperature of 180° C. and Reaction Time of 0.5 h 285 g of trioctylamine ($[CH_3(CH_2)_7]_3N$; 0.8 mol, 98%; Sigma-Aldrich Chemie GmbH, Taufkirchen, Germany; catalog # T81000) were mixed with 123.4 g of solid 3-BrPA (0.8 mol, 97%; Sigma-Aldrich Chemie GmbH, Taufkirchen, Germany; catalog #101281) in a three-necked glass reactor in a molar ratio of 1:1 at room temperature and atmospheric conditions. The reaction mixture was heated to 180° C. under continuous stirring with a magnetic stirring bar at a speed of 500 rpm. After the reaction mixture reached a constant temperature of 180° C., the reaction products were semi-batchwise removed under reduced pressure (90-100 mbar). The liquid products were condensed and collected in an ice-cooled flask, and the gaseous by-products were routed to the off-gas. After a reaction time of 0.5 h, the collected distillate was analyzed via off-line $^1$H NMR (JEOL ECX 400 MHz). $^1$H qNMR analysis of the product mixture gave an acrylic acid yield of about 90 mol % and selectivity of more than about 90 mol %.

Example 56—Acrylic Acid Synthesis from 3-BrPA with Trioctylamine (TOA) at Temperature of 80° C. and Reaction Time of 1 h 34.3 g of trioctylamine ($[CH_3(CH_2)_7]_3N$; 0.095 mol, 98%; Sigma-Aldrich Chemie GmbH, Taufkirchen, Germany; catalog # T81000) were mixed with 15.04 g of solid 3-BrPA (0.095 mol, 97%; Sigma-Aldrich Chemie GmbH, Taufkirchen, Germany; catalog #101281) in a three-necked glass reactor in a molar ratio of 1:1 at room temperature and atmospheric conditions. The reaction mixture was heated to 80° C. under continuous stirring with a magnetic stirring bar at a speed of 500 rpm and a reflux condenser. The gaseous by-products were routed to the off-gas. After a reaction time of 1 h, the collected distillate was analyzed via off-line $^1$H NMR (JEOL ECX 400 MHz). $^1$H qNMR analysis of the product mixture gave an acrylic acid yield of about 96 mol %.

The foregoing description is given for clearness of understanding only, and no unnecessary limitations should be understood therefrom, as modifications within the scope of the invention may be apparent to those having ordinary skill in the art.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making acrylic acid comprising the steps:
   a. contacting a feed stream comprising lactic acid, lactide, or mixtures thereof with a first molten salt catalyst in a first reactor at a first reaction temperature and a first reaction time to produce a first stream comprising 2-bromopropionic acid (2-BrPA);
   b. contacting said 2-BrPA with a second molten salt catalyst in a second reactor at a second reaction temperature and a second reaction time to produce a second stream comprising 3-bromopropionic acid (3-BrPA) and said acrylic acid; and
   c. contacting said 3-BrPA with an amine in a third reactor at a third reaction temperature and a third reaction time to produce a third stream comprising said acrylic acid;
   wherein said first molten salt catalyst comprises a bromide anion ($Br^-$); wherein said second molten salt catalyst comprises a $Br^-$; wherein said acrylic acid of said second stream is combined with said acrylic acid of said third stream into a production stream of said acrylic acid; and wherein said acrylic acid in said production stream has an overall acrylic acid yield and an overall acrylic acid selectivity.

2. The method of claim 1, wherein said first molten salt catalyst comprises a protic ionic liquid (PIL).

3. The method of claim 2, wherein said PIL comprises 3-methyl-1-(4-butane sulfonic acid) imidazolium bromide ([MIMBS]Br).

4. The method of claim 3, wherein said [MIMBS]Br has a molar ratio to said lactic acid, lactide, or mixtures thereof in said feed stream of about 3:1.

5. The method of claim 3, wherein said first molten salt catalyst further comprises a dilute HBr aqueous solution.

6. The method of claim 5, wherein said dilute HBr aqueous solution comprises 20 mmol HBr.

7. The method of claim 3, wherein said first reaction temperature ranges from about 80° C. to about 160° C.

8. The method of claim 7, wherein said first reaction temperature ranges from about 100° C. to about 140° C.

9. The method of claim 8, wherein said first reaction temperature is about 120° C.

10. The method of claim 3, wherein said first reaction time ranges from about 2 h to about 10 h.

11. The method of claim 10, wherein said first reaction time ranges from about 3 h to about 8 h.

12. The method of claim 11, wherein said first reaction time is about 5 h.

13. The method of claim 3, wherein said 2-BrPA is produced in said first reactor at a yield of more than about 30 mol % and with a selectivity of more than about 90 mol %.

14. The method of claim 13, wherein said 2-BrPA is produced in said first reactor at a yield of more than about 45 mol % and with a selectivity of more than about 92 mol %.

15. The method of claim 14, wherein said 2-BrPA is produced in said first reactor at a yield of about 60 mol % and with a selectivity of more than about 95 mol %.

16. The method of claim 1, wherein said second molten salt catalyst comprises an ionic liquid (IL); and wherein said IL comprises 1-ethyl-3-methylimidazolium bromide ([EMIM]Br).

17. The method of claim 16, wherein said second reaction temperature ranges from about 80° C. to about 200° C.

18. The method of claim 17, wherein said second reaction temperature ranges from about 100° C. to about 180° C.

19. The method of claim 18, wherein said second reaction temperature is about 160° C.

20. The method of claim 16, wherein said second reaction time ranges from about 1 h to about 48 h.

21. The method of claim 20, wherein said second reaction time ranges from about 2 h to about 24 h.

22. The method of claim 21, wherein said second reaction time ranges from about 3 h to about 20 h.

23. The method of claim 22, wherein said second reaction time is about 20 h.

24. The method of claim 22, wherein said second reaction time is about 3 h.

25. The method of claim 1, wherein said second molten salt catalyst comprises an ionic liquid (IL); and wherein said IL comprises tetrabutylphosphonium bromide ([PBu$_4$]Br).

26. The method of claim 25, wherein said 3-BrPA is produced in said second reactor at a yield of about 79 mol % and with a selectivity of about 89 mol %.

27. The method of claim 25, wherein said [PBu$_4$]Br and said 2-BrPA have a molar ratio of about 9:1.

28. The method of claim 27, wherein said 3-BrPA and said acrylic acid are produced in said second reactor at a combined yield of more than about 80 mol %.

29. The method of claim 27, wherein said combined yield of said 3-BrPA and said acrylic acid produced in said second reactor is more than about 95 mol %.

30. The method of claim 1, wherein said amine is trioctylamine (TOA).

31. The method of claim 30, wherein said third reaction temperature is about 180° C.; and wherein said third reaction time is about 0.5 h.

32. A method of making acrylic acid comprising the steps:
a. contacting a feed stream comprising lactic acid, lactide, or mixtures thereof with a first molten salt catalyst in a first reactor at a reaction temperature of about 120° C. and a reaction time of about 5 h to produce a first stream comprising 2-bromopropionic acid (2-BrPA) at a yield of about 60 mol % and with a selectivity of more than 95 mol %;
b. contacting said 2-BrPA with a second molten salt catalyst in a second reactor at a reaction temperature of about 160° C. and a second reaction time of about 20 h to produce a second stream comprising 3-bromopropionic acid (3-BrPA) at a yield of about 79 mol % and with a selectivity of about 89 mol %, and said acrylic acid at a yield of about 3 mol %; and
c. contacting said 3-BrPA with a trioctylamine (TOA) in a third reactor at a third reaction temperature of about 180° C. and a third reaction time of about 0.5 h to produce a third stream comprising said acrylic acid at a yield of about 90 mol % and with a selectivity of more than about 90 mol %;
wherein said first molten salt catalyst comprises 3-methyl-1-(4-butane sulfonic acid) imidazolium bromide ([MIMBS]Br); wherein said [MIMBS]Br has a molar ratio to said lactic acid, lactide, or mixtures thereof of about 3:1; wherein said molten salt catalyst further comprises a 20 mmol HBr aqueous solution; wherein said second molten salt catalyst comprises tetrabutylphosphonium bromide ([PBu$_4$]Br); wherein said [PBu$_4$]Br and said 2-BrPA have a molar ratio of about 1:1; wherein said acrylic acid of said second stream is combined with said acrylic acid of said third stream into a production stream of said acrylic acid; and wherein said acrylic acid in said production stream has an overall acrylic acid yield of about 43 mol % and an overall acrylic acid selectivity of about 76 mol %.

33. A method of making acrylic acid comprising the steps:
a. contacting a feed stream comprising lactic acid, lactide, or mixtures thereof with a first molten salt catalyst in a first reactor at a reaction temperature of about 120° C. and a reaction time of about 5 h to produce a first stream comprising 2-bromopropionic acid (2-BrPA) at a yield of about 60 mol % and with a selectivity of more than 95 mol %;
b. contacting said 2-BrPA with a second molten salt catalyst in a second reactor at a reaction temperature of about 180° C. and a second reaction time of about 3 h to produce a second stream comprising 3-bromopropionic acid (3-BrPA) at a yield of about 52 mol % and with a selectivity of about 54 mol %, and said acrylic acid at a yield of about 45 mol %; and
c. contacting said 3-BrPA with a trioctylamine (TOA) in a third reactor at a third reaction temperature of about 180° C. and a third reaction time of about 0.5 h to produce a third stream comprising said acrylic acid at a yield of about 90 mol % and with a selectivity of more than about 90 mol %;
wherein said first molten salt catalyst comprises 3-methyl-1-(4-butane sulfonic acid) imidazolium bromide ([MIMBS]Br); wherein said [MIMBS]Br has a molar ratio to said lactic acid, lactide, or mixtures thereof of about 3:1; wherein said molten salt catalyst further comprises a 20 mmol HBr aqueous solution; wherein said second molten salt catalyst comprises tetrabutylphosphonium bromide ([PBu$_4$]Br); wherein said [PBu$_4$]Br and said 2-BrPA have a molar ratio of about 9:1; wherein said acrylic acid of said second stream is combined with said acrylic acid of said third stream into a production stream of said acrylic acid; and wherein said acrylic acid in said production stream has an overall acrylic acid yield of about 55 mol % and an overall acrylic acid selectivity of about 83 mol %.

* * * * *